United States Patent
Iniewski et al.

(10) Patent No.: US 11,344,266 B2
(45) Date of Patent: May 31, 2022

(54) CALIBRATION METHODS FOR IMPROVING UNIFORMITY IN X-RAY PHOTON COUNTING DETECTORS

(71) Applicant: REDLEN TECHNOLOGIES, INC., Saanichton (CA)

(72) Inventors: Krzysztof Iniewski, Coquitlam (CA); Elmaddin Guliyev, Vancouver (CA); Conny Hansson, Victoria (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 0 days.

(21) Appl. No.: 17/019,750

(22) Filed: Sep. 14, 2020

(65) Prior Publication Data
US 2021/0121143 A1 Apr. 29, 2021

Related U.S. Application Data

(60) Provisional application No. 62/900,779, filed on Sep. 16, 2019.

(51) Int. Cl.
*A61B 6/00* (2006.01)
*G01N 23/046* (2018.01)

(52) U.S. Cl.
CPC .......... *A61B 6/4241* (2013.01); *A61B 6/5205* (2013.01); *A61B 6/585* (2013.01); *G01N 23/046* (2013.01)

(58) Field of Classification Search
CPC ..... A61B 6/4241; A61B 6/5205; A61B 6/585; G01N 23/046
See application file for complete search history.

(56) References Cited

U.S. PATENT DOCUMENTS

| 6,590,957 | B1 * | 7/2003 | Warburton | ........... A61B 6/4241 378/5 |
| 7,208,739 | B1 * | 4/2007 | Yanoff | .................... G01T 1/171 250/363.09 |
| 10,393,891 | B2 | 8/2019 | Iniewski et al. | |

(Continued)

OTHER PUBLICATIONS

Knoll, G.F., "Radiation Detection and Measurement," Dec. 1999, 3$^{rd}$ Edition, Publisher: John Wiley, New York, ISBN: 0-471-07338-5.

(Continued)

*Primary Examiner* — Blake C Riddick
(74) *Attorney, Agent, or Firm* — The Marbury Law Group PLLC

(57) ABSTRACT

Various aspects include methods for use in X-ray detectors for adjusting count measurements from pixel detectors within a pixelated detector module to correct for the effects of pileup events that occur when more than one photon is absorbed in a pixel detector during a deadtime of the detector system. In various embodiments, count measurements may be obtained at two different X-ray tube currents, from which the detector system deadtime may be calculated based on the two count measurements and a ratio of the two X-ray tube currents. Using the calculated deadtime, a pileup correction factor may be determined appropriate for the behavior of the detector system in response to pileup events. The pileup correction factor may be applied to pixel detector count values after the counts have been corrected for pixel-to-pixel differences using a flat field correction.

7 Claims, 13 Drawing Sheets

(56) References Cited

U.S. PATENT DOCUMENTS

| | | | |
|---|---|---|---|
| 10,396,109 B2 | 8/2019 | Iniewski et al. | |
| 2005/0123090 A1* | 6/2005 | Heismann | G01T 1/171 378/19 |
| 2007/0076842 A1* | 4/2007 | Tkaczyk | A61B 6/4042 378/5 |
| 2007/0076848 A1* | 4/2007 | Walter | A61B 6/032 378/98.8 |
| 2008/0260094 A1* | 10/2008 | Carmi | A61B 6/482 378/19 |
| 2009/0039273 A1* | 2/2009 | Tkaczyk | G01T 1/249 250/370.06 |
| 2010/0027738 A1* | 2/2010 | Carmi | G01T 1/17 378/19 |
| 2011/0155899 A1* | 6/2011 | Dror | G01T 1/247 250/252.1 |
| 2014/0314211 A1* | 10/2014 | Zou | A61B 6/482 378/207 |
| 2014/0328466 A1* | 11/2014 | Proksa | H03K 5/2463 378/62 |
| 2015/0160355 A1* | 6/2015 | Wang | A61B 6/585 378/19 |
| 2015/0223766 A1* | 8/2015 | Besson | A61B 6/035 378/5 |
| 2015/0282778 A1* | 10/2015 | Kato | A61B 6/488 378/5 |
| 2016/0033654 A1* | 2/2016 | Tamura | G01T 1/2985 378/98.9 |
| 2016/0203620 A1* | 7/2016 | Zou | A61B 6/4241 378/19 |
| 2017/0231584 A1* | 8/2017 | Konno | G01N 23/046 378/5 |
| 2017/0290555 A1 | 10/2017 | Iniewski et al. | |
| 2017/0322319 A1 | 11/2017 | Iniewski et al. | |
| 2017/0325756 A1* | 11/2017 | Teshigawara | G01T 1/40 |
| 2018/0098746 A1* | 4/2018 | Kato | G21K 1/10 |
| 2018/0204356 A1* | 7/2018 | Xia | A61B 6/482 |
| 2018/0211417 A1* | 7/2018 | Miyazaki | G06T 7/11 |
| 2018/0300909 A1* | 10/2018 | Tamura | A61B 6/4266 |
| 2019/0000409 A1* | 1/2019 | Tamura | A61B 6/4241 |
| 2019/0021685 A1* | 1/2019 | Kojima | A61B 6/585 |
| 2019/0021687 A1* | 1/2019 | Kato | A61B 6/4241 |
| 2019/0200945 A1* | 7/2019 | Tsuyuki | A61B 6/547 |
| 2019/0313993 A1* | 10/2019 | Zhou | A61B 6/502 |
| 2019/0383956 A1 | 12/2019 | Guliyev et al. | |
| 2020/0116874 A1 | 4/2020 | Prekas et al. | |
| 2020/0132866 A1 | 4/2020 | Taherion et al. | |
| 2020/0150297 A1 | 5/2020 | Iniewski et al. | |
| 2020/0193654 A1* | 6/2020 | Yanoff | G06T 11/006 |
| 2020/0319121 A1* | 10/2020 | Daerr | A61B 6/542 |
| 2020/0408929 A1* | 12/2020 | Wang | G01T 1/17 |

OTHER PUBLICATIONS

Siu, C. et al., "Application Specific Integrated Circuits (ASICs) for Spectral Photon Counting," Spectral, Photon Counting Computed Tomography (pp. 251-278), Jun. 2020, DOI: 10.1201/9780429486111-14.

U.S. Appl. No. 16/844,484, filed Apr. 9, 2020, Redlen Technologies, Inc.

U.S. Appl. No. 16/875,133, filed May 15, 2020, Redlen Technologies, Inc.

U.S. Appl. No. 16/894,063, filed Jun. 5, 2020, Redlen Technologies, Inc.

U.S. Appl. No. 16/931,800, filed Jul. 17, 2020, Redlen Technologies, Inc.

* cited by examiner

| Tube Current (mA) | True Count $T$ | Average Measured Count $M$ | Count Loss (%) | Uniformity Metric (%) |
|---|---|---|---|---|
| 1 | 1,000 | 984 | 1.6% | 1.8% |
| 10 | 10,000 | 9,992 | 13.8% | 1.5% |
| 25 | 25,000 | 17,846 | 28.6% | 1.2% |
| 100 | 100,000 | 38,477 | 61.5% | 0.7% |

FIG. 8A

| Tube Current (mA) | True Count $T$ | Average Measured Count $M$ | Count Loss (%) | Uniformity Metric (%) |
|---|---|---|---|---|
| 1 | 800-1,000 | 923 | 1.5% | 9.2% |
| 10 | 8,000-10,000 | 8,032 | 13.0% | 8.1% |
| 25 | 20,000-25,000 | 16,809 | 27.2% | 7.0% |
| 100 | 80,000-100,000 | 37,133 | 59.8% | 4.0% |

FIG. 8B

| Tube Current (mA) | True Count $T$ | Average Measured Count $M$ | Uniformity Metric (%) | Corrected Uniformity Metric (%) |
|---|---|---|---|---|
| 1 | 800-1,000 | 923 | 9.2% | 0.1% |
| 10 | 8,000-10,000 | 8,032 | 8.1% | 1.2% |
| 25 | 20,000-25,000 | 16,809 | 7.0% | 2.6% |
| 100 | 80,000-100,000 | 37,133 | 4.0% | 5.9% |

FIG. 8C

| Tube Current (mA) | True Count $T$ | Average Measured Count $M$ | Uniformity Metric (%) | Corrected Uniformity Metric (%) |
|---|---|---|---|---|
| 1 | 800-1,000 | 923 | 9.2% | 0.1% |
| 10 | 8,000-10,000 | 8,032 | 8.1% | 0.24% |
| 25 | 20,000-25,000 | 16,809 | 7.0% | 0.5% |
| 100 | 80,000-100,000 | 37,133 | 4.0% | 1.1% |

FIG. 8D

| Tube Current (mA) | Raw Un-Calibrated Uniformity Metric (%) | One-step Calibrated Uniformity Metric (%) | Two-step Calibrated Uniformity Metric (%) |
|---|---|---|---|
| 1 | 6.6% | 0% | 0.9% |
| 10 | 5.5% | 3.1% | 2.7% |
| 25 | 4.4% | 4.9% | 3.3% |
| 100 | N/A | N/A | N/A |

FIG. 9

CALIBRATION METHODS FOR IMPROVING UNIFORMITY IN X-RAY PHOTON COUNTING DETECTORS

FIELD

The present application relates generally to radiation detectors for X-ray imaging systems.

BACKGROUND

In X-ray imaging systems, an X-ray source emits a fan-shaped beam toward an object, such as piece of baggage at an airport scanner or patient in a medical diagnostic clinic, or any other biological or non-biological object that is being imaged in Non-Destructive Testing (NDT) in food inspection for example. The X-ray beam is attenuated by the object and subsequently detected by a detector element, such as a Cadmium Zinc Telluride (CdZnTe, or CZT) detector. Other direct conversion detectors such as Cadmium Telluride (CdTe), Gallium Arsenide (GaAs), or Silicon (Si), or any indirect director based on scintillator material may also be used in X-ray imaging systems. Image slices collected by scanning the object may, when joined together, produce 2- or 3-dimensional cross-section images of the target object.

In typical X-ray imaging systems, a detector array that includes a number of detector elements may each produce a dedicated electrical signal that indicates the level of attenuation received by each detector element. The electrical signals may be transmitted to a data processing card for analysis. Finally, using image reconstruction techniques an image is produced. The intensity of the attenuated beam received by each detector element is dependent upon the attenuation of the X-ray beam by the object. For example, when scanning a human body, bone turns up white, air turns up black, and tissues and mucous turn up in shades of gray.

Calibration of fabricated semiconductor sensors, like those made out of CdZnTe, and their corresponding imaging modules, remains a challenge and can be error prone process. This increases the cost of selling the sensors/modules for the sensor manufacturers and reduces the time of operating X-ray computed tomography (CT) imaging systems for operators of imaging systems due to frequent calibration required.

SUMMARY

Various embodiments include methods for calibrating pixelated radiation detectors to address pixel count non-uniformity taking into account pileup effects. Various embodiments include method for correcting the output from pixel detectors within a pixelated detector of an imaging X-ray system that may include determining a pileup correction factor based on count measurements obtained at two different X-ray tube current levels, and applying the pileup correction factor to pixel detector count measurements obtained while imaging an object to obtain pixel detector counts corrected for pileup effects.

In some embodiments, determining a pileup correction factor based on count measurements obtained at two different X-ray tube current levels may include obtaining first count measurements in the pixel detectors while operating the imaging X-ray system at a first X-ray tube current level, obtaining second count measurements in the pixel detectors while operating the imaging X-ray system at a second X-ray tube current level in which the second X-ray tube current level is different from the first X-ray tube current level, using the first and second count measurements and a ratio of the first X-ray tube current level to the second X-ray tube current level to determine a deadtime of the pixelated detector, and determining the pileup correction factor based upon the determine deadtime of the pixelated detector and a pileup model appropriate to a response of the pixelated detector to pileup events. In some embodiments, the pileup correction factor may be equal to (1−M×τ), in which M is the measured counts to be corrected and τ is the determined deadtime of the pixelated detector. In some embodiments, applying the pileup correction factor to pixel detector count measurements obtained while imaging an object to obtain pixel detector counts corrected for pileup effects may include applying a flat field correction to the pixel detector count measurements obtained while imaging the object to obtain pixel detector counts corrected for pixel-to-pixel variability, and applying the pileup correction factor to the pixel detector counts corrected for pixel-to-pixel variability to obtain pixel detector counts corrected for pileup effects. Some embodiments may further include determining the flat field correction by obtaining dark-field noise measurements of the pixel detectors with the X-ray tube off, and determining the flat field correction based on the dark-field noise measurements and the first count measurements.

BRIEF DESCRIPTION OF THE DRAWINGS

The accompanying drawings are presented to aid in the description of embodiments of the disclosure and are provided solely for illustration of the embodiments and not limitation thereof.

FIGS. 8A-8D are tables showing effects of X-ray flux (as a function of X-ray tube current) on count loss and an inter-pixel uniformity metric in pixelated detectors based on simulations with different presumptions and calibration factors.

FIG. 9 is a table summarizing results of applying one-step and two-step calibration methods of various embodiments on inter-pixel detector uniformity metric.

DETAILED DESCRIPTION

Figure 1:
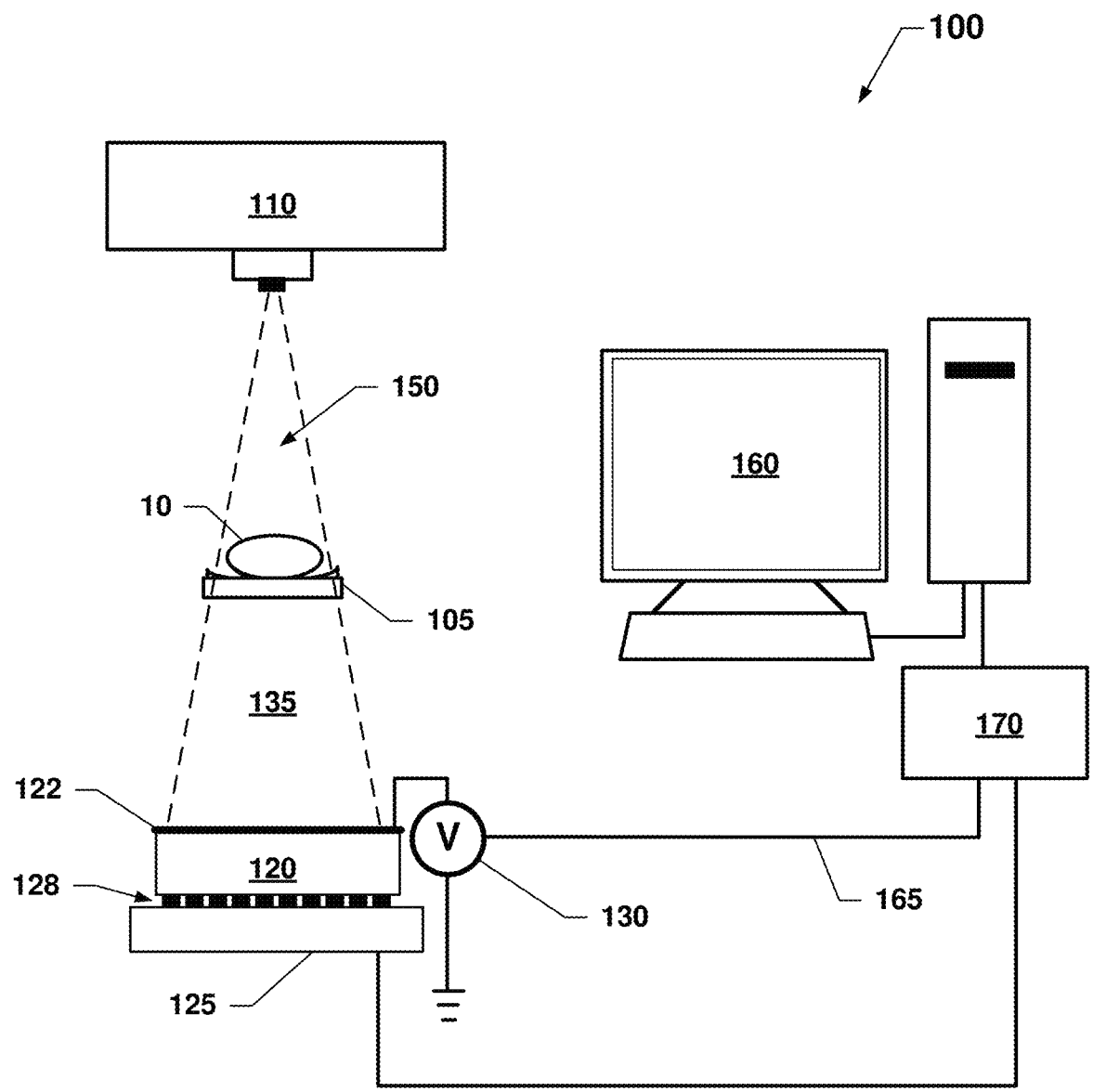
FIG. 1 is a block diagram of an X-ray imaging system suitable for use with various embodiments of the present disclosure.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

Various embodiments improve on imaging X-ray detectors by providing additional calibration operations to account for pixel count non-uniformity taking into account the effects of pileup detection events. Various embodiments include method for correcting the output from pixel detectors within a pixelated detector of an imaging X-ray system that may include determining a pileup correction factor based on count measurements obtained at two different X-ray tube current levels, and applying the pileup correction factor to pixel detector count measurements obtained while imaging an object to obtain pixel detector counts corrected for pileup effects.

In some embodiments, determining a pileup correction factor based on count measurements obtained at two different X-ray tube current levels may include obtaining first count measurements in the pixel detectors while operating the imaging X-ray system at a first X-ray tube current level, obtaining second count measurements in the pixel detectors while operating the imaging X-ray system at a second X-ray tube current level in which the second X-ray tube current level is different from the first X-ray tube current level, using the first and second count measurements and a ratio of the first X-ray tube current level to the second X-ray tube current level to determine a deadtime of the pixelated detector, and determining the pileup correction factor based upon the determine deadtime of the pixelated detector and a pileup model appropriate to a response of the pixelated detector to pileup events. In some embodiments, the pileup correction factor may be equal to $(1-M \times \tau)$, in which M is the measured counts to be corrected and $\tau$ is the determined deadtime of the pixelated detector. In some embodiments, applying the pileup correction factor to pixel detector count measurements obtained while imaging an object to obtain pixel detector counts corrected for pileup effects may include applying a flat field correction to the pixel detector count measurements obtained while imaging the object to obtain pixel detector counts corrected for pixel-to-pixel variability, and applying the pileup correction factor to the pixel detector counts corrected for pixel-to-pixel variability to obtain pixel detector counts corrected for pileup effects. Some embodiments may further include determining the flat field correction by obtaining dark-field noise measurements of the pixel detectors with the X-ray tube off, and determining the flat field correction based on the dark-field noise measurements and the first count measurements.

CdZnTe pixel detectors in pixelated detector module never have exactly the same counting response, even if they are of the same size. The differences may be due to material imperfections (e.g., Tellurium inclusions in CdZnTe), anode contact non-uniformities, or difference in ASIC readout channels which although designed to be identical undergo usually semiconductor manufacturing variations. The difference in counts can be calibrated out in a calibration procedure called a flat-field correction similar to visible light pixelated detectors. However, in pixelated CdZnTe detector arrays the flat-field correction faces some additional challenges that are not present in standard visible light digital imaging.

First, the area of all pixel detectors (and corresponding voxels) are almost never the same due to various geometrical consideration (sensor edges and corners, anti-scatter grid ASG placement, or special imaging considerations). If the pixel areas differ, as is typically the case, the differences in pixel response can be large. The flat-filed correction would require some modifications to counter such effects.

However, the correction problem is more complicated when the detector module operates in different count rare/flux levels. As the X-ray photon count rate increases, the pixel detectors enter the pileup regime in which the actual rate of photon absorptions in the detector, referred to herein as the input count rate ("ICR" in the figures), is no longer proportional to the measured detection counts, referred to herein as the output count rate ("OCR" in the figures). This pileup property introduces additional errors when performing flat-field correction. The subject of this invention is to prose a new calibration scheme that removes and/or at least reduces these errors.

Flat-field correction is a technique used to improve image quality in digital imaging. The goal is to remove artifacts from two-dimensional (2-D) images that are caused by variations in the pixel-to-pixel sensitivity of the detector and/or by distortions in the optical path. The flat-field correction is a standard calibration procedure in everything from pocket digital cameras to giant telescopes that use pixelate detectors, and is being used in X-ray imaging as well.

In X-ray imaging, the acquired projection images generally suffer from fixed-pattern noise, which is one of the limiting factors of image quality. Fixed-pattern noise may stem from beam inhomogeneity, gain variations of the detector response in each pixel detector due to inhomogeneities from pixel to pixel in the photon conversion yield, losses in charge transport, charge trapping, and variations in the performance of the readout. Also, the detector may accumulate dust and/or scratches on its surface, resulting in systematic patterns among different pixel detectors in acquired X-ray projection images.

In X-ray CT imaging systems, fixed-pattern noise is known to significantly degrade the achievable spatial resolution and generally leads to ring or band artifacts in the reconstructed images. Fixed pattern noise can be removed using a flat field correction.

In conventional flat field correction methods, images in the form of counts from each pixel detector within the radiation detector array are obtained with the X-ray beam turned off, and then again with the X-ray beam turned on but without an intervening sample or filter. Image data obtained with the X-ray beam turned on and without an intervening sample or filter are referred to as flat fields (F). Image data obtained with the X-ray beam turned off are referred to as dark fields (D). Based on the acquired flat and dark fields, the measured projection images (P) can be normalized to new images (N) according to this formula:

$$N=(P-D)/(F-D) \quad [\text{Eq}1]$$

This formula is applied on a pixel-by-pixel basis. Thus N, P, D and F are matrices of values corresponding to counts obtained from individual pixel detectors within the pixelated radiation detector. Measurements of dark fields and flat fields may be obtained at the time of manufacture as an initial calibration, and may be performed each time that the imaging system is used as a runtime calibration. The flat field correction method normalizes pixel count data to account for pixel-to-pixel variations in sensitivity and efficiency in detecting X-ray photons due to manufacturing differences and locations of individual pixel detectors within the array (e.g., edge and corner pixel detectors), operating conditions (e.g., temperature), the age of the detector.

In performing X-ray analysis, two basic terms are defined with respect to the number of photons are being received by the X-ray sensor. The input count rate is a measure of the number of photons impinging on the sensor surface per unit time and is typically expressed in millions of counts per second per square millimeter ($mm^2$) Similarly, the output count rate is a measure of the number of photons that separately detected counted by the sensor and is typically expressed in millions of counts per second per $mm^2$ Typically, the output count rate is smaller than the input count rate, and the ratio of the output count rate with respect to the input count rate is typically referred to as detector sensitivity (sometimes detector efficiency).

One of the main reasons for the difference between input count rate and output count rate is the pileup effect that occurs in pixel detectors at high X-ray tube current levels. Pileup effects are caused by multiple photons interacting with a pixel detector within a detection time interval. A pileup event happens when two (or more) photon detection signals overlap during the temporal resolution of the detector, resulting in one (or more) of the photon detections not being recognized and counted. The loss of counts (and the resulting impact on sensitivity/efficiency) due to pileup effects can be a major problem in X-ray image analysis, particularly in applications that use a high X-ray flux.

While the flat field correction works well for correcting systemic variability in sensitivity and efficiency among pixel detectors, it does not account for effects that vary with the photon flux. In particular, the flat field correction fails to address pixel-to-pixel variability resulting from pileup effects. This is because the flat field correction assumes static variability among pixel detectors that can be addressed by a scaler adjustment to the count recorded by each pixel detector. Pileup effects are not static because the effect varies with photon flux as will be explained in more detail below. Various embodiments overcome the limitations of the flat field correction by applying another correction factor that is determined based on flat field images obtained at two different X-ray photon flux levels to compensate for flux-dependent pixel-to-pixel variability.

FIG. 1 is a functional block diagram of an example ionizing radiation imaging system in accordance with various embodiments. The illustrated example ionizing radiation, is a CT imaging system 100 that includes an X-ray source 110 (i.e., a source of ionizing radiation), and a radiation detector 120. The CT imaging system 100 may additionally include a support structure 105, such as a table or frame, which may rest on the floor and may support an object 10 to be scanned. The support structure 105 may be stationary (i.e., non-moving) or may be configured to move relative to other elements of the CT imaging system 100. The object 10 may be all or a portion of any biological (e.g., a human patient) or non-biological (e.g., luggage) object to be scanned.

The X-ray source 110 is configured to deliver ionizing radiation to the radiation detector 120 by emitting an X-ray beam 135 toward the object 10 and the radiation detector 120. After the X-ray beam 135 is attenuated by the object 10, the beam of radiation 135 is received by the radiation detector 120.

The radiation detector 120 may be controlled by a high voltage bias power supply 130 that selectively creates an electric field between an anode 122 and cathode 128 pair coupled thereto. The radiation detector 120 may include CdZnTe material disposed between the anode 122 and cathode 128 and thus configured to be exposed to the electrical field therebetween. A read-out application specific integrated circuit (ASIC) 125 coupled to the anode 122 and cathode 128 pair may receive signals (e.g., charge or current) from the anode 122 and be configured to provide data to and by controlled by a control unit 170.

The control unit 170 may be configured to synchronize the X-ray source 110, the read-out ASIC 125, and the high voltage bias power supply 130. The control unit 170 may be coupled to and operated from a computing device 160. Alternatively, the computing device 160 and the control unit 170 may be integrated together as one device.

The object 10 may pass between the X-ray source 110 and the radiation detector 120 or alternatively the object may remain stationary while the X-ray source 110 and the radiation detector 120 move relative to the object 10. Either way, the radiation detector 120 may capture incremental cross-sectional profiles of the object 10. The data acquired by the radiation detector 120 may be passed along to the computing device 160 that may be located remotely from the radiation detector 120 via a connection 165. The connection 165 may be any type of wired or wireless connection. If the connection 165 is a wired connection, the connection 165 may include a slip ring electrical connection between any structure supporting the radiation detector 120 and a stationary support part of the support structure 105, which supports any part (e.g., a rotating ring). If the connection 165 is a wireless connection, the radiation detector 120 may contain any suitable wireless transceiver to communicate data with another wireless transceiver that is in communication with the computing device 160. The computing device 160 may include processing and imaging applications that analyze each profile obtained by the radiation detector 120, and a full set of profiles may be compiled to form two-dimensional images of cross-sectional slices of the object 10.

Various alternatives to the design of the CT imaging system 100 of FIG. 1 may be employed to practice embodiments of the present disclosure. CT imaging systems may be designed in various architectures and configurations. For example, a CT imaging system may have a helical architecture. In a helical CT imaging scanner, the X-ray source and detector array are attached to a freely rotating gantry. During a scan, a table moves the object smoothly through the scanner creating helical path traced out by the X-ray beam. Slip rings enable the transfer of power and data on and off the rotating gantry. In other embodiments, the CT imaging system may be a tomosynthesis CT imaging system. In a tomosynthesis CT scanner, the gantry may move in a limited rotation angle (e.g., between 15 degrees and 60 degrees) in order to detect a cross-sectional slice of the object. The tomosynthesis CT scanner may be able to acquire slices at different depths and with different thicknesses that may be constructed via image processing.

The detector array of a CT imaging system may include an array of radiation detector elements, referred to herein as pixel detectors. The signals from the pixel detectors may be processed by a pixel detector circuit, which may sort detected photons into energy bins based on the energy of each photon or the voltage generated by the received photon. When an X-ray photon is detected, its energy is determined and the X-ray photon count for its associated energy bin is incremented. For example, if the detected energy of an X-ray photon is 24 kilo-electron-volts (keV), the X-ray photon count for the energy bin of 20-40 keV may be incremented. The number of energy bins may range from one to several, such as two to six. In an illustrative example, an X-ray photon counting detector may have four energy bins: a first bin for detecting photons having an energy between 20 keV and 40 keV, a second bin for detecting photons having an energy between 40 keV and 60 keV, a third bin for detecting photons having an energy between 60 keV and 80 keV, and a fourth bin for detecting photons having an energy above 80 keV. The greater the total number of energy bins, the better the material discrimination.

In CT imaging systems, a scanned object is exposed to an X-ray beam and attenuated photons from the X-ray beam are detected and counted by individual radiation pixel detectors in a detector array. When an object (e.g., the object 10) is loaded in a CT imaging system, the X-ray beam may be heavily attenuated, and the number of photons detected by the detector array may be orders of magnitude less than the number of photons emitted from an X-ray source. When obtaining the flat fields data for determining the flat field collection, the radiation detector is exposed to a direct X-ray beam without an intervening object located inside the CT imaging system. In such cases, the X-ray photon count rates in the CT imaging system may reach values of 100 million counts per second per square millimeter (Mcps/mm$^2$) or more. The detector array may be capable of detecting such a wide range of photon count rates.

It should be noted that various embodiments of imaging radiation detectors and methods of processing signals from such detectors, may be used in other types of ionizing radiation imaging systems, such as Single Photon Emission Computed Tomography (SPECT) imaging systems, stationary X-ray imaging systems, non-destructive testing and inspection imaging systems, etc.

Figure 2:
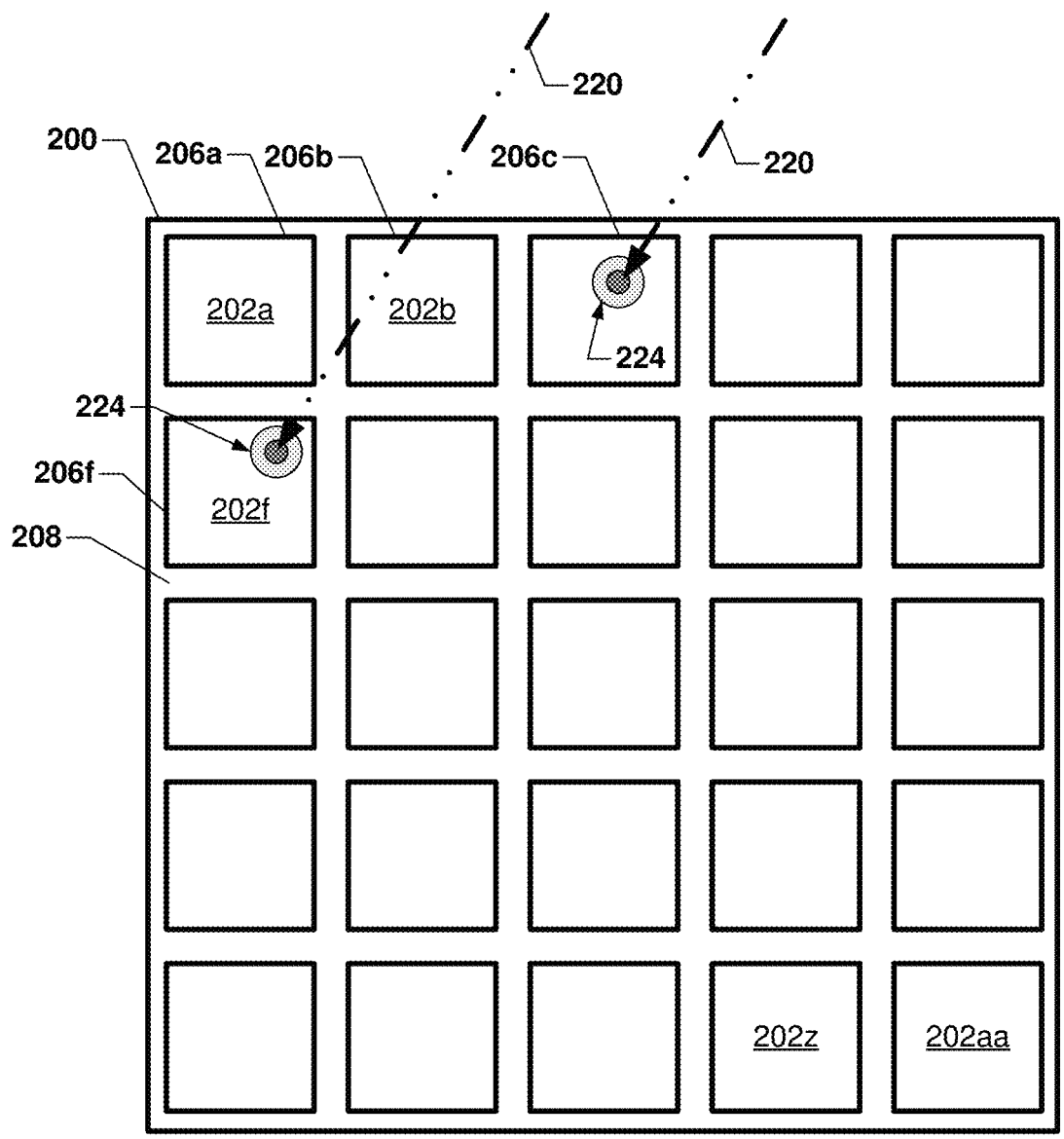
FIG. 2 is a conceptual top view diagram of a semiconductor pixel radiation detector illustrating X-ray interactions.

FIG. 2 is a top view of a portion of a pixelated radiation detector array 200 showing the plurality of pixel detectors 202a-202aa formed by the anodes 206a, 206b positioned on the CZT semiconductor crystal 208. As described above, when an X-ray 220 interacts with atoms within the CZT semiconductor crystal 208, the cloud of ejected electrons 224 are gathered on the nearby anode 206c, 206f and recorded as a count. Further, the number of electrons 224 (i.e., charge) collected on the anode 206c, 206f is reflective of the energy of the incoming photon, and thus a measurement of the energy (or spectrum) of the detected photon can be determined from the charge or current detected on the anodes.

Figure 3A:
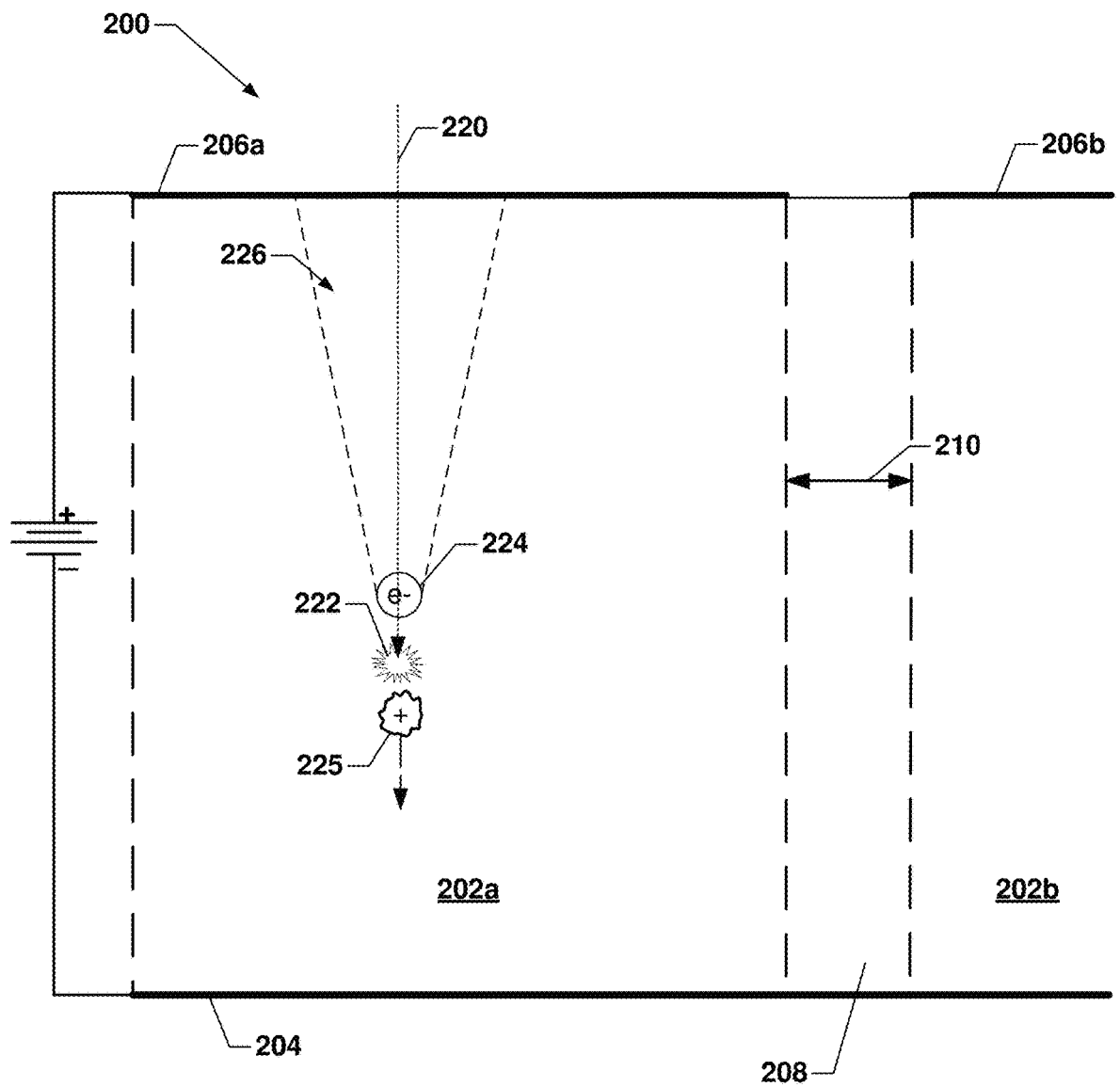
FIG. 3A is a conceptual cross section view diagram of a semiconductor pixel radiation detector illustrating an X-ray absorption and mechanisms for detecting and measuring the energy of the detected X-ray.

As an X-ray photon enters the CZT sensor volume of a detector and interacts with the atoms constituting that sensor it will deposit some, or all, of its energy. FIG. 3A illustrates a cross-sectional view of two pixel detectors 202a, 202b within a CZT radiation detector array 200. Such a detector 200 may include a sheet of CZT semiconductor crystal 208 on which are applied to a cathode 204 and the anodes 206a, 206b that define each pixel 202a, 202b. The anodes 206a, 206b may be spaced apart by an inter-pixel gap 210. In typical radiation detector arrays 200, the thickness of the CZT semiconductor crystal 208 may range from 1 mm to 20 mm, the anodes 206a, 206b may have a side dimension of 0.1 mm to 3 mm, and the inter-pixel gap 210 may range from 0.01 mm to 0.5 mm.

When an X-ray 220 is absorbed via a photoelectric effect event 222 by an electron of an atom within the CZT semiconductor crystal 208, the energy of the X-ray photon is transferred to an ejected electron (not shown) that quickly slows down by ionizing nearby atoms thus generating a cloud of electrons 224 ejected into the conduction band of the semiconductor along the path of travel. The range of a photoelectron in CZT depends on the energy carried off by that electron. Each ejected electron creates a corresponding hole 225 of positive charge. The clouds of electrons (and holes) generated by a photoelectron are not uniform in charge density, because electron-hole production increases towards the end of the track of the photoelectron. A voltage is applied between the cathode 224 and anodes 206a, 206b causes the electrons 224 to drift to the anode 206a where they are collected as a signal as described above. Holes 225 similarly migrate towards the cathode 204. Diffusion and charge repulsion forces cause the electron cloud to expand (as shown at 226) by the time the electrons reached the anode 206a.

The term "cloud" is used to highlight the fact that the physical size of the electron charge is not a point but approximately a sphere with a certain radius. Each X-ray photon absorbed in the CZT detector generates several thousands of electrons, so even the initial charge has finite physical dimensions. The number of generated electrons can be estimated by dividing the incoming photon energy by the CZT ionization energy of 4.64 eV. For example, an X ray photon with an energy of 140 keV will produce about 30,000 electrons in the conduction zone, collectively carrying a charge of approximately 4.8 femto coulombs (fC).

In photon counting computed tomography, like in any high-count X-ray detector system, to accurately differentiate between two photon detection events, a minimum time separating those events is needed. This minimum separation time is referred to as the deadtime "τ" of the system. As the detector needs to accommodate the time required for the charge cloud 226 to migrate to the anode 206a before recording the gathered charge into a count, the pixel detector circuitry is typically configured with a deadtime timer that it is triggered when a charge signal on the anode is first detected and controls when the charge on the anode should be registered as a signal indicative of the energy of the detected photon. In a typical detector, a threshold circuit coupled to each anode 206 may start such a timer when the charge on the anode exceeds a certain minimum threshold. The deadtime τ provides sufficient time for the electron cloud produced by the photon interaction to move to the anode and for the read-out electronics to measure the induced charge and the reset to detect the next photon interaction. The deadtime in X-ray imaging detectors is brief, on the order of a few tens of nanoseconds. In a typical example, pixelated detector circuitry may have a deadtime τ of approximately 16 ns. Without providing this deadtime before recording a detection signal, the measured charge on the anode would not reflect the full charge in the cloud of electrons generated by absorption of the photon, and as a result the full energy of the incident photon may not be determined. This is particularly true for the photons that interact with the detector material far from the anode.

While the deadtime is necessary to obtain an accurate measure of detected photon energies, the deadtime provides an interval during which two photons can be absorbed by the detector, resulting in a pileup event. The rate at which pileup events occur in any pixel detector is approximately equal to the rate of X-ray photons absorbed by the detector (i.e., the input count rate) times the deadtime. Since the deadtime is very brief, such as ~16 ns, there are very few pileup events when the X-ray flux is low. However, in a high X-ray flux application, there is a significant probability that a second (or third) photon will be absorbed in the detector pixel during the deadtime, resulting in a pileup detection event. This can be a significant problem in any of a number of X-ray imaging systems (e.g., a CT scanner).

Figure 3B:
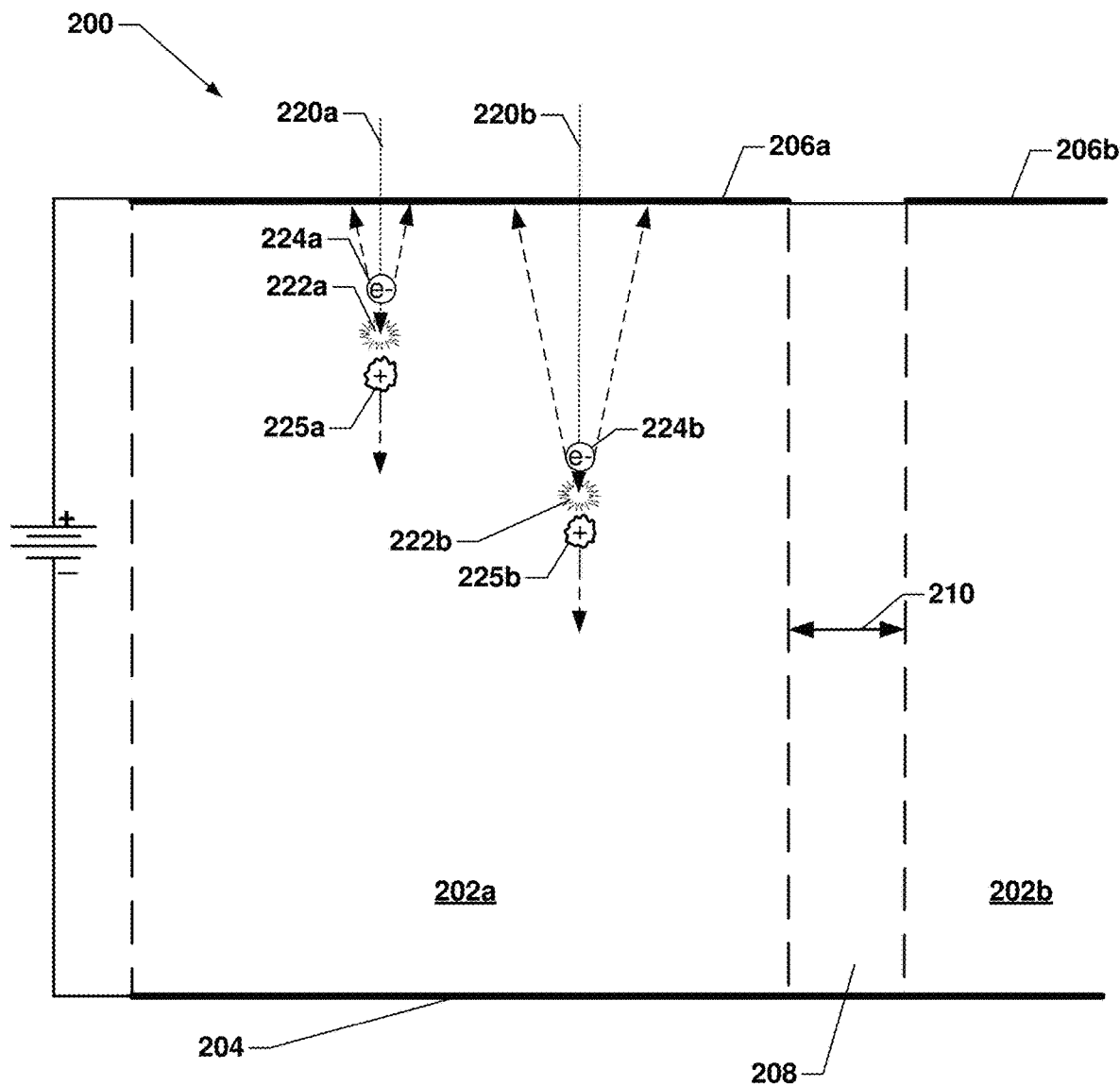
FIG. 3B is a conceptual cross section view diagram of a semiconductor pixel radiation detector illustrating an X-ray "pileup" detection event.

An example of a pileup detection event is illustrated in FIG. 3B. In this example, a first X-ray photon 220a is absorbed in a first photoelectric event 222a, resulting in a first electron cloud 224a that migrates toward the anode 206a and a first hole cloud 225a that migrates toward the cathode 204. Before the end of the deadtime, a second X-ray photon 220b is absorbed in a second photoelectric event 222b, resulting in a second electron cloud 224b that migrates toward the anode 206a and a second hole cloud 225a that migrates toward the cathode 204. Thus, by the end of the deadtime, the total charge accumulated by the pixel anode 206a will be that of the first electron cloud 224a and at least a portion of the second electron cloud 224b, resulting in a greater charge read by the CSA, and thus a higher energy output signal by the CSA than the energy of either incoming photon 220a, 220b. Thus, if treated as a single detection event, the resulting detection will be of one photon count instead of two with an energy measurement (i.e., charge accumulated on the anode) greater than that of either incident photon.

One way to detect pileup conditions is to measure output count rate-input count rate characteristics. When the X-ray flux is relatively low while operating the X-ray tube at low current levels, the relationship between the input count rate, controlled by the X-ray tube current, and the output count rate is effectively linear. This is because at a low X-ray flux, the probability of pileup events occurring in any one pixel detector is relatively low. Said another way, the rate of pileup events is low, and therefore the number of lost counts is also low. At medium X-ray current levels, the curve of the output count rate versus X-ray tube current level starts to deviate from linearity as the increase in X-ray flux increases the rate of pileup events, and thus the rate of lost counts, in pixel detectors. At high X-ray tube currents, when the X-ray flux is high, the current of output count rate versus X-ray tube current can saturate as pileup events begin to dominate photon detections within the pixel detectors.

Radiation detectors can be characterized by their response to pileup events depending upon the trigger mechanism for the detection circuitry (also referred to as read-out electronics). The behavior of a detector system in a pileup event (i.e., when one or multiple photon absorption events occur in a pixel detector within the deadtime τ triggered by a previous absorption event) is dictated by the architecture of the system and can depend on the physical processes in the sensor, or delays in the pulse processing chain or readout electronics.

In one type of X-ray detector (i.e., detector materials and detection circuitry), the deadtime triggered by detection of a charge on the anode from a first photon absorption runs for a fixed period of time (i.e., the deadtime), regardless of whether additional photons are absorbed in the pixel detector during that deadtime. Such detectors are less sensitive to saturation due to pileup effects because the detector is available to detect photons at the end of the fixed deadtime. Such detectors are said to exhibit "non-paralyzable behavior" because the detector is not paralyzed by pileup effects at very high X-ray flux levels.

In another type of X-ray detector (i.e., detector materials and detection circuitry), the deadtime is triggered by each detection of a charge on the anode regardless of when each photon is detected. Such detectors are sensitive to saturation due to pileup effects because the deadtime during which counts are lost may be extended by subsequent photon detections. Such detectors are said to exhibit "paralyzable behavior."

Figure 4:
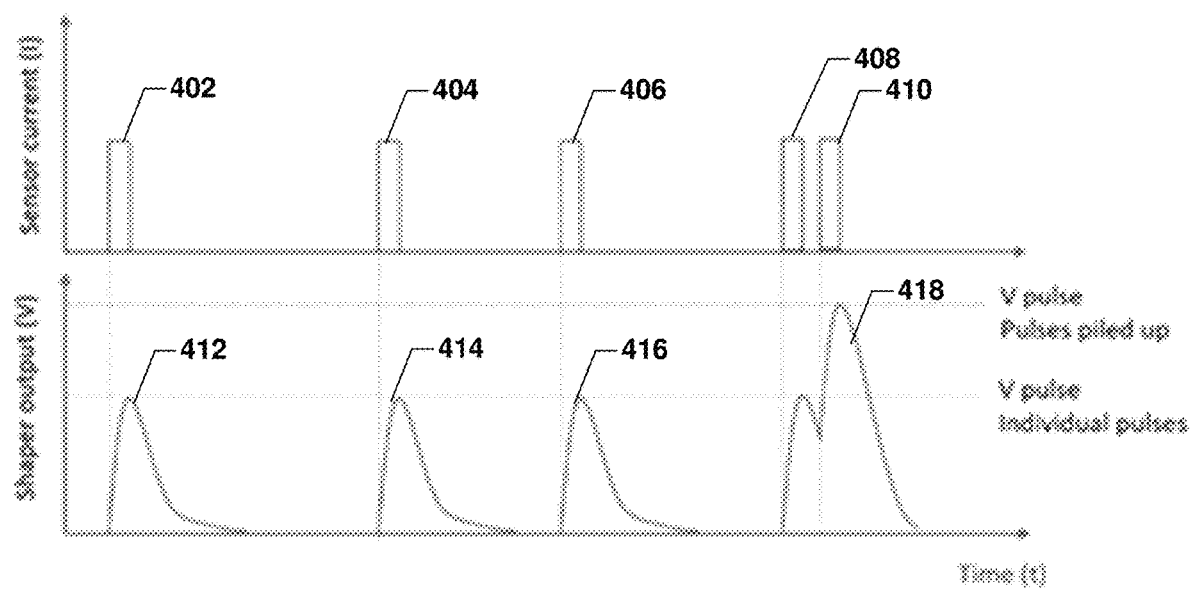
FIG. 4 is a graph contrasting non-pileup detection events from a pileup detection event and the resulting effect on the measured pulse.

Two closely related phenomena are usually considered during these conditions: pileup and count loss. Pileup usually refers to when the pulse being induced on the readout electronics from one event temporally interacts with the pulse from another event. This is illustrated in FIG. 4, where the top graph illustrates the electron cloud generated by photons interacting with the anode (i.e. the photon absorption events), and the bottom graph shows the corresponding voltage output signal observed for these events at the output of the read-out electronics (e.g., a "shaper" circuit). FIG. 4 illustrates how the timing of photon absorption events 402-410 can affect the voltage pulse output 412-420 by the shaper circuit. So long as the photon absorption events 402, 404, 406 are separated in time by more than the deadtime, the voltage output signal 412, 414, 416 associated with each absorption event can be distinguished by the read-out electronics, as illustrated in the first three photon absorption events shown in FIG. 4. However, when two or more photon absorption events 408, 410 occur within the deadtime and thus temporally interact, the detector circuitry cannot distinguish the two events (i.e., a pileup event occurs) resulting in a convolution of the two voltage signals into a single combined voltage output signal 418.

FIG. 4 illustrates that a pileup event results in two effects. First, the two voltage signals are counted as one photon detection (i.e., count), thus resulting in one count loss. Second, the combined voltage signal 418 that is detected is incorrectly determined to be greater (i.e., associated with a higher energy photon) than it should be for either one of the two overlapping photon absorption events 408, 410, thus resulting in an error in the determined photon energy. For non-energy discriminating detectors, this second effect would not be an issue, only the first effect of a count loss would. However, for an energy discriminating detector, such as the used for spectral photon counting for computed tomography (PCCT), the second effect would lead to a distorted measured spectral response.

The pileup effect shown in FIG. 4 is a traditional analogue electronic illustration of this effect, where the time constant of the shaper circuit often sets the limitation for pileup onset (pileup resolution time) and dictates the maximum count rates allowable before spectral distortion occurs. However, if a peak hold circuit following on from the shaper is used to hold the peak value for read out, for example, and a second event occurs before the peak hold value has been read out, the highest peak height pulse would eventually be read out. This can lead to both a loss in count and a distorted spectral response, as described above, without the pulses necessarily being temporally overlapping. Depending on the particular implementation of the readout electronics modeling of the pileup effects can be quite different.

When discussing deadtime count loss in detector systems, two idealized behaviors are usually referenced—detector systems that become paralyzing or saturated at high X-ray flus, and detector systems that are not non-paralyzed at high X-ray flux. The two types of X-ray detection systems may be characterized by a paralyzable model and a non-paralyzable model that sets out to correlate the deadtime τ, the true count T (i.e., the number of photons absorbed in the detector per unit time), and measured counts M (i.e., the number of counts output by the readout electronics per unit time) for a detector system. These two models relate the three-primary metrics of deadtime τ, true count T, and measured counts M to each other. The difference between the true count T and measured count M is the count loss. The main difference between the non-paralyzable and the paralyzable model is in how the detector system reacts when a second event occurs within the deadtime of the first event. The response of systems adhering to both these models to the same incoming count rate scenario is illustrated in FIG. 5.

Figure 5:
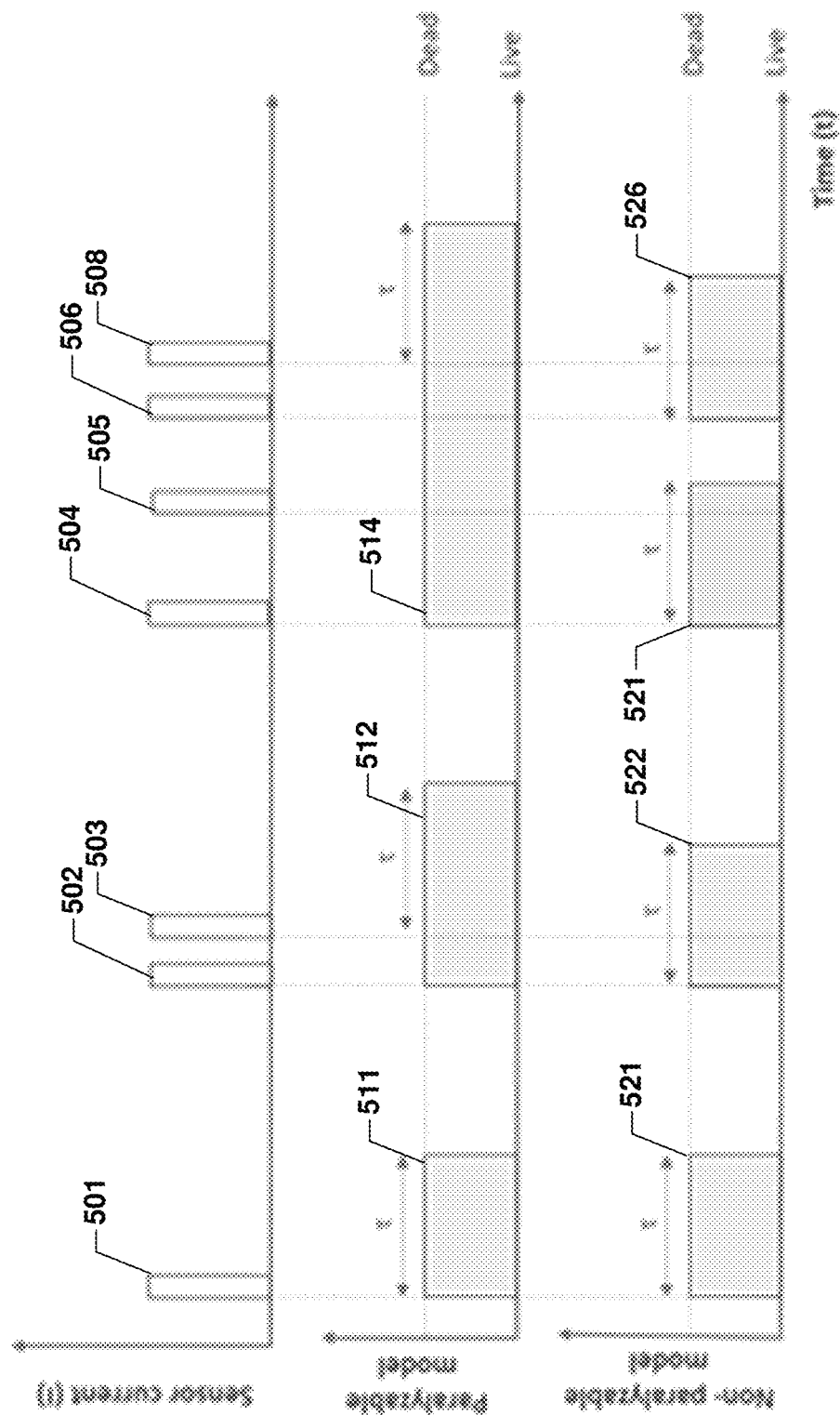
FIG. 5 is a graph illustrating the effects of pileup detection events for X-ray detectors that are "paralyzable" and X-ray detectors that are "non-paralyzable."

FIG. 5 illustrates the response of an X-ray detector that exhibits paralyzable behavior (middle graph) and the response of an X-ray detector that exhibits non-paralyzable behavior (bottom graph) to the same incoming photon detection event sequence (top graph). As shown in FIG. 5, at low count rates, illustrated by photon detection event 501, both types of detector systems accurately determine the count rate because pileup events are rare.

However, as count rates increase, and thus the average interval between two photon detection events decreases, the behaviors of the two types of X-ray detectors begin to differ. For example, in response to a single pileup event in which two photon absorption events 502, 503 occur within the deadtime, the deadtime 512 of the detector triggered by the first photon absorption event 502 is extended by detection of the second photon absorption event 503. Thus, the detector system would remain non-responsive to subsequent photon absorption events until the deadtime has elapsed from the time when the second photon absorption event was registered. In contrast, the detector exhibiting non-paralyzable behavior has a fixed duration deadtime 521 triggered by the first photon absorption event 502. Both types of detectors failed to recognize the second photon absorption event 503, and thus have a count loss equal to 1. However, the detector exhibiting non-paralyzable behavior will be responsive to subsequent photon absorption events as soon as the deadtime has elapsed from the time when the first photon absorption event 502 was registered.

The behaviors of these two types of detector systems diverge as the rate of pileup events increases with increasing X-ray flux. This is illustrated by the responses of the two types of detector systems to multiple photon absorption events occurring close together in sequence as illustrated in photon absorption events 504-508. Once the X-ray flux, and thus the photon absorption rate, is high enough, the detector exhibiting paralyzable behavior will consistently have photon absorption events happening within the deadtime following a previous photon absorption event, and the detector system would exhibit an extended nonresponsive deadtime 514. Thus, in the illustrated example, four photon absorption events 504-508 would register as a single count 514, resulting in a count loss of three. At a high enough rate of photon absorption events, a detector exhibiting paralyzable behavior might never come out of a non-responsive mode, i.e. the non-responsive period 514 could be indefinite, resulting in a measured count of 1 regardless of the number of photon absorption events.

In contrast, a detector exhibiting non-paralyzable behavior would lose a count for a photon absorption event 505 occurring during the deadtime 521 triggered by a first photon absorption event 504, but would then become responsive to a subsequent photon absorption event 506 resulting in a count and another deadtime 526, although it would lose a count for another photon absorption event 508 during that second deadtime. As can be seen from this illustration, the count rate measured by a detector exhibiting non-paralyzable behavior under extremely high X-ray flux conditions would be given by the time that counts are measured (e.g., an exposure time) divided by the length of the fixed deadtime.

It should be noted that the non-paralyzable and paralyzable models are idealized behaviors, and any real detector system, like a CZT readout detector module, may have a response behavior that falls somewhere between these two extremes as dictated by the response of the detector system architecture and readout electronics implementation.

For a detector system exhibiting non-paralyzable behavior, the amount of time the detector system is non-responsive is a set value, as illustrated in FIG. 5, and the total amount of non-responsive time in any measured interval is set by the measured number of counts and the deadtime, i.e. M×τ. As such, the rate of count loss is given by T×M×τ. Considering that the rate of count loss also can be written as T−M, this yields the equation T−M=T×M×τ. Solving this equation for the true count rate T (which is the desired output for a radiation detector) yields the following non-paralyzable model equation:

$$T=M/(1-(M\times\tau)) \quad [\text{Eq2}]$$

As can be seen in FIG. 5, the non-responsive period for a detector exhibiting paralyzable behavior is not always a set value. However, it can be shown that the distribution of intervals between random events occurring at an average rate is given by the following equation:

$$P(\Delta t)d\Delta t=T\times e^{\hat{}}(T\times\Delta t)d\Delta \quad [\text{Eq3}]$$

where the left-hand term is the probability of observing an interval within dΔt of Δt. Since any two events occurring within a deadtime of each other in a detector exhibiting paralyzable behavior would end up with a non-responsive period exceeding the minimum deadtime τ, integrating the above expression from τ to ∞, and multiplying for the true count rate T, yields the following paralyzable model equation:

$$M=T\times e^{\hat{}}(-T\times\tau) \quad [\text{Eq4}]$$

Figure 6:
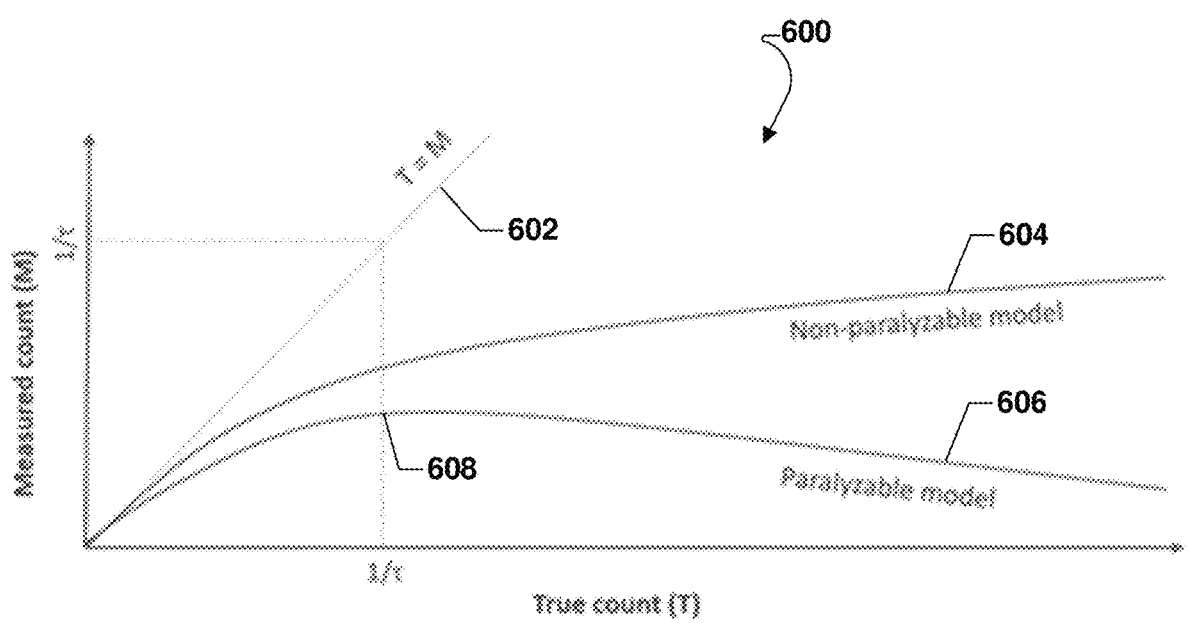
FIG. 6 is a graph showing an example of the effects of pileup events on measured count rates for paralyzable detectors and non-paralyzable detectors as a function of the true count rate (i.e., X-ray flux).

The variation in true count vs. the measured count for an ideal detector (i.e., a detector in which the measured count equals the true count or T=M), a detector following the non-paralyzing model, and a detector following the paralyzing model is illustrated in the graph shown in FIG. 6.

As shown in FIG. 6, at very low photon absorption rates the three models line up. As the photon absorption rate increases, however, the probability of two photon absorption events occurring in a pixel detector within the deadtime increases, and the non-paralyzing or paralyzing natures of the two types of detector system become significant and influence the measured counts. For a detector exhibiting paralyzable behavior, operating at rates exceeding the peak measured count (i.e., $T \sim 1/\tau$) introduces an ambiguity in trying to determine the true count, since any one measured count M could correspond to two values of true count T, which can be hard to differentiate. Additionally, operating under conditions in which the count loss exceeds 30-40% is not advisable because small measured count variations would correspond to large variations in true count. As such, any error in the measurement will result in a large error in the accuracy of the estimated true count.

In order to correct for counts lost due to pileup effects it is first necessary to correct or calibrate an imaging X-ray detector system for the sensitivity variability among pixel detectors due to manufacturing and other differences. This may be accomplished during factory acceptance testing of detector modules performed at the factory before shipping to the customer for purposes of characterizing the detector module. In general, there are two main properties of imaging pixel detectors that are important in PCCT modules: how uniformly the pixel detectors respond to X-ray photons and how stable that response is. A first category of factory acceptance tests is related to count uniformity, which is referred to as Count Uniformity. The second category of factory acceptance tests is related to pixel stability, both in steady-state conditions (constant flux) and during dynamic changes when X-ray flux changes rapidly. This category is referred to as Count Stability. The count uniformity and Count stability of each pixel detector may be compared to a minimum acceptance standard, and if the number of non-confirming pixel detectors within a single detector array exceeds a critical value, the detector array may be rejected and scrapped. Finally, if a detector array passes factory acceptance tests (i.e., the number of non-confirming pixel detectors (NCPs) is smaller than the critical value), a list of non-conforming pixel detectors may be generated, analyzed, and sent to the customer along with the detector array. In operation, outputs from non-conforming pixel detectors may be ignored in an imaging system implementing the detector array.

In an ideal world, X-ray detection modules will have all pixel detectors exposed to the same X-ray signal producing exactly the same counts. Clearly that is not possible, due to manufacturing variability and other factors. In most cases customer specific pixel patterns will not have uniform voxel size—and the count uniformity measurements will have to normalize to compensate for difference in pixel detector sizes. The imaging X-ray detection module undergoes complex calibration sequence inside the CT scanner, or similar X-ray imaging systems, and that calibration process can remove many count non-uniformities using flat-field corrections and other more elaborate calibration using phantom measurements. However, standard flat field correction is not sufficient for CT scanner quality requirements due to pileup effects described above.

Uniformity specifications are formulated after noisy, non-responsive or over-responsive pixel detectors have been eliminated by considering them NCPs. In other words, uniformity specifications are applied to only good pixel detectors, which should comprise anywhere from 95% to 99% of all the pixel detectors. Various metrics can be used for that purpose and industry has selected a simple metric of standard deviation (std_dev) as a primary uniformity evaluation. The metric of standard deviation (std_dev) relative to the mean (std_dev/mean) is used below to compare various calibration schemes (standard and according to various embodiments) in a variety of configurations (all pixel detectors the same and pixel size varying).

The uniformity specification requires that the standard deviation of pixel detector counts with respect to the mean is less than a certain number, typically less than 5%, but less than 3% is highly desired. These calculations are performed after prior NCPs have been eliminated. The calculations are performed on a per energy bin basis for all energy bins, and for a number of X-ray tube current settings, for example 1 mA, 10 mA, 25 mA and 100 mA. If the detector module does not satisfy this std_dev/mean<5% criteria, the detector module is disqualified and rejected.

CT scanners require extreme count stability within the imaging X-ray detector modules. Although count stability is only loosely related to count uniformity, it is worthwhile to consider CT basics to shed more light on the problem. The Hounsfield unit (HU) scale is a linear transformation of the original linear attenuation coefficient measurement into one in which the radiodensity of distilled water at standard pressure and temperature (STP) is defined as zero Hounsfield units (HU), while the radiodensity of air at STP is defined as −1000 HU. In a voxel with average linear attenuation coefficient $\mu$, the corresponding HU value is therefore given by:

$$HU = 1000 * (\mu - \mu_{water}) / (\mu_{water} - \mu_{air}) \quad [\text{Eq5}]$$

where $\mu_{water}$ and $\mu_{air}$ are respectively the linear attenuation coefficients of water and air. Thus, a change of 1 Hounsfield unit (HU) represents a change of 0.1% of the attenuation coefficient of water since the attenuation coefficient of air is nearly zero.

In an ideal world one would like to see counts to be stable within 1 HU. In practice people argue whether 1 HU artifact is worth considering, however, 3 HU is considered to be high enough to matter. These numbers pertain to structured artifacts, like rings and circles especially (lesion-mimicking). Rings are the main problem because small differences in a pixel detector calibration cause rings. Beam hardening artifacts are routinely above 3 HU, but radiologists know about them, so they are acceptable. Metal artifacts are much higher, around 100-1000 HU, and CT scanner manufacturers try to eliminate them.

The critical level of stability required for imaging X-ray detector modules is 3 HU, or 0.3%, although it is desired to be as close to 1 HU, which is 0.1%. To ensure sufficiently stable PCCT detector module behavior manufacturers test stability in various scenarios. These stability tests are easier to perform and interpret if pixel detector count is uniform, such as the calibrated count does not change between the pixel detectors and all levels of count rates are required.

To illustrate the uniformity challenges, consider a Gaussian distribution of the average count 1,000 for a 10 by 10-pixel matrix, with pixel detectors of 330 um by 330 um size. In this example, 1,000 counts corresponds approximately to a 1 mA X-ray tube current, with the tube placed 30 cm away from the detector surface imaged for 1 ms (view time). The standard deviation-to-mean ratio for the whole detector array of 100 pixel detectors is about 1.7%, which is the expected ratio for properly designed and manufactured detection module. The table shown in FIG. 8A shows the results of calculations based on these assumptions, particularly that all of the pixel detectors are exactly the same size.

Referring to FIG. 8A, if there were no pileup effects, the data generated by the detector module at an X-ray tube current of 10 mA would be exactly the same as with an X-ray tube current of 1 mA, except scaled by a factor of 10 as shown in the true count T column of the table. The corresponding std_dev/mean of the detector array would still be 1.7%. To illustrate the effect of the pileup the non-paralyzable model given by [Eq2] with a deadtime of 16 ns was used to estimate the average measured count, which is listed the Average Measured Count M column of the table shown in FIG. 8A. As a result of the pileup effects the counts do not reach the previous 10,000 counts level, but exhibit an average 13.8% count loss, and as a result the corresponding std_dev/mean is slightly reduced to 1.5%. The trend continues at 25 mA. As a result of the pileup effects the counts do not reach 25,000 level but experience on average 28.6% count loss. The corresponding std_dev/mean is slightly reduced down to 1.2%. Finally, at an X-ray tube current of 100 mA the measured counts do not reach 100,000 level and exhibit on average 61.5% count loss. The corresponding std_dev/mean is slightly reduced down to 0.7%.

The output count rate count increases non-linearly with the input count rate as expected. In addition, somewhat unexpectedly the std-dev/mean ratio also improves as the rate of pileup events increases. One simple explanation for this is that pileup effects act as an equalizer. Pixel detectors that have higher counts enter pileup earlier hence suffer pileup degradation at lower true count rates, resulting in their count rates being closer to the count rates of pixel detectors having lower count rates. In the extreme when the pileup rate is very high, the measured count M will be given by 1/deadtime, so all pixel detectors will have exactly the same count, resulting in a std_dev/mean equal to zero. In practice, that extreme count rate is not possible to be realized experimentally. In addition, the deadtime values themselves would have some manufacturing spread unless calibrated very precisely at the readout electronics level.

In the calculations leading to the results shown in FIG. 8A, all of the pixel detectors have the same area and address only inherent differences in count rates due to manufacturing imperfections. In reality, the pixel detectors differ in their sizes and corresponding collections voxels for various reasons. For example, a frequent requirement in CdZnTe based radiation detection system is a need to maintain pixel pitch between neighboring sensors. This can only be accomplished by making the edge pixel detectors smaller in order to accommodate non-zero width crystal to crystal gaps.

The effects on count loss and uniformity due to pixel detectors having different sizes may be illustrated by running a simulation based on the assumption described above plus assuming that all edge pixel detectors in the 10×10 pixel array have 20% less area, hence systematically less 20% counts. In addition, the four corner pixel detectors with have 36% less area and corresponding system counts. The results of calculations based on these assumptions are listed in the table that is shown in FIG. 8B. Due to the lower counts in the first edge and some corners effects, the corresponding std_dev/mean is significantly increased to 9.2% at an X-ray tube current of 1 mA. This is as expected as there are two classes of pixel detectors, normal ones, and the ones with reduce areas and counts. These simulations were then repeated for X-ray tube currents of 10, 25, and 100 mA. The results of these simulations are summarized in the table shown in FIG. 8B.

A first important difference to note is the impact on absolute values on non-uniformity metrics. The standard deviation is varied from 1.8% to 0.7% assuming pixel detectors the same size is summarized in the table shown in FIG. 8A, but various from 9.2% to 4.0% when edges and corners were present as shown in the table that is FIG. 8B.

Second, the uniformity varies more when the difference in size pixel detectors due to the edge and corner detectors is taken into consideration. These values exceed the std_dev<3% qualifying metric, and therefore the detector module would fail a practical factory acceptance test. Thus, further corrections for the pixel area is required.

The next step is to apply a standard flat-field correction to the generated results at X-ray tube currents of 1, 10, 25 and 100 mA, as would be done typically in practice. Again, the flat field correction is obtained by determining correction factors for each of the pixel detectors that will result in inconsistent counts across the detector, thereby compensating for any pixel-to-pixel differences, such as pixel detector area/volume. The result of applying a standard flat field correction to the simulation results at each of the different X-ray tube currents is summarized in the table that is shown in FIG. 8C.

The results summarized in FIG. 8C show that after the flat-field correction, the uniformity values are better, as expected. In particular, at an X-ray tube current of 1 mA all non-uniformities have been calibrated out and the std_dev/mean metric is close to zero. However, the flat-field correction does not rectify pixel-to-pixel differences with increasing X-ray flux, and at an X-ray tube current of 100 mA the std_dev/mean is worse than prior to the flat field correction. This effect can be explained by the pileup effects discussed above, because at high-count rates, the edge and corner pixel detectors are over-corrected by the flat field correction compared to the regular (i.e., interior) pixel detectors. This illustrates that a better means of calibrating for non-uniformities when the pileup effect is required.

The next step is to apply the two-point pileup correction procedure of the various embodiments to the results following the flat field correction. The two-point pileup correction procedure relies on using the pileup model described above with reference to equations 2 to 4, which characterizes the difference between the measured output count and the input count rate (i.e., the actual photon absorption rate or true counts T) due to pileup effects. Using the non-paralyzable model given by [Eq2], an appropriate calibration factor for detectors exhibiting the non-paralyzable behavior can be determined by measuring the counts for exposures of the same duration (i.e., for the same exposure time) at two different X-ray tube current levels, and thus two different X-ray flux levels. Applying the non-paralyzable model for pileup effects, the two count measurements lead to the following two equations:

$$T1 = M1/(1-(M1 \times \tau)) \quad [\text{Eq. 6}]$$

$$T2 = M2/(1-(M2 \times \tau)) \quad [\text{Eq. 7}]$$

where M1 and M2 are the measured counts and T1 and T2 are the true counts at the two different X-ray tube currents (i.e., the input count rate times the exposure time). At this stage, T1 and T2 and the deadtime τ are not known. The deadtime τ may be known approximately as it may be a design factor in the detector circuitry. However, the deadtime τ differs from chip to chip due to manufacturing variability, and may vary with operating temperature and/or age. Therefore, to obtain an accurate compensation for pileup effects, the deadtime τ may be determined as part of a periodic calibration procedure.

With three unknowns in these equations, one normally needs three equations to solve for the deadtime τ. However, the true counts T1 and T2 scale with the current of the X-ray tube, so if count measurements M1 and M2 are taken at two different X-ray tube currents, such as 1 mA and 10 mA, the ratio R of the true counts T1 and T2 should be the ratio of the two X-ray tube currents, such as T2/T1=10 mA/1 mA=10. With this additional condition, equations [Eq6] and [Eq7] can be easily solved for the deadtime τ based on the two measured counts M1 and M2. For example, having measured counts M1 and M2 taken at two X-ray tube currents that differ by a factor of R, the deadtime τ may be calculated as $$\tau = [M2(1-1/R)]^{-1} - [M1(R-1)]^{-1} \qquad [\text{Eq. 8}]$$

Solving for the deadtime τ enables calculating correction factors (1−M×τ) to normalize counts in pixel detectors to account for pileup effects in detectors that follow the non-paralyzable model. Specifically, the factor (1−M×τ) may be applied to the pixel detector count values that have been normalized by the flat-field correction to provide an X-ray image data set corrected for pileup effects. Thus, by taking two X-ray images or otherwise obtaining the output counts for a given interval at two (or more) X-ray tube currents in a calibration step, and using that information to determine a correction factor, X-ray images can be adjusted to account for distortion effects due to pileup cannot be addressed by the flat field correction factor.

This correction factor may be applied to the counts measured for each pixel detector with each exposure, in which M is the count determined for the pixel detector after the flat field correction has been applied. Thus, knowing the deadtime τ a correction factor may be individually determined for each pixel detector based upon that detector's counts.

In a similar manner, correction factors may be determined that are suitable for detectors that exhibit the paralyzable behavior, or combinations of the paralyzable and non-paralyzable behaviors. For example, as noted in equation 4, the measured counts M are related to the true counts by and exponential relationship. Due to the increasing count loss due to pileup effects at a high true count rates in detectors following the paralyzable model, as illustrated in FIG. 4, pileup correction factors may depend upon the magnitude of X-ray flux (and thus X-ray tube current). For example, the paralyzable model curve in FIG. 4 shows that the output count rate is similar to the output count rate of a non-paralyzable model detector at all low input count rates, begins to depart from the output count rate of a non-paralyzable model as the input count rate increases, reaches a maximum when the input count rate T is approximately equal to the inverse of the deadtime τ (where a correlation factor would be equal to e), and then decreases with increasing input count rate. For example, at low true count rates, a correction factor similar to the non-paralyzable model factor of (1−M×τ) may be applied to account for pileup effects. Near a maximum output count rate (i.e., when the true count rate is approximately equal to the inverse of the deadtime τ a constant correction factor of e may be used. At higher true count rates, a correction factor based on equation 4 may be used.

Thus, for detectors that exhibit the paralyzable behavior, different correction factors may be determined for the different count rate regimes, with the proper correction factor applied based upon an estimate of the X-ray flux or a measure of the rate of pileup events. For example, pileup events can be detected by detecting photon energies that exceed the maximum energy of X-rays expected to be produced by the X-ray tube. Operating true count rate regimes in which the output count rate is maximized or beyond may be recognized when pileup detection count rate equals or exceeds half of the total count rate, as can be inferred from FIG. 4.

Applying the pileup correction procedures of various embodiments to apply a pileup correction factor to simulation results following the flat field corrections for detectors following the non-paralyzable model yields results listed in the table shown in FIG. 8D. As can be seen in the results listed in the table shown in FIG. 8D, application of the 2-point correction factor to take into account pileup effects results in significantly better pixel-to-pixel uniformity than for the flat-field correction alone listed in the table shown in FIG. 8C. Up to 5 times improvement at very high count rate has been obtained. This analysis presumed the analysis would result in an error in the determined deadtime of 2 ns, which is about 12% of the presumed 16 ns deadtime. Determining the deadtime using such procedures may have error rates better than 2 ns, in which case the errors given in the table shown in FIG. 8D would be even smaller.

Testing of a typical pixilated detector applying the procedures of the various embodiments confirmed the analysis described above, with the results of the testing shown in the table that is FIG. 9. As this table shows, the measured uniformity metric improves with X-ray tube current due to the pileup equalization effect discussed above, but remains in a range that is unacceptable for precise imaging, which should be less than 3-4%. Significant improvements are obtained with the standard one-step calibration as shown in the third column of the table shown in FIG. 9, with perfect calibrated results at an X-ray tube current of 1 mA. Again, this is to be expected as an X-ray tube current of 1 mA was the basis for determining the flat field calibration. However, at large X-ray tube current levels (i.e., high X-ray flux levels) the uniformity metric is severely distorted due the pileup effects as discussed above. Although test data at an X-ray tube current of 100 mA, which would be typical for an industrial CT scanner, were not obtained, the results at an X-ray tube current of 25 mA were beyond the acceptable level and expected to be significantly worse at 100 mA and beyond.

Figures 7A, 7B:
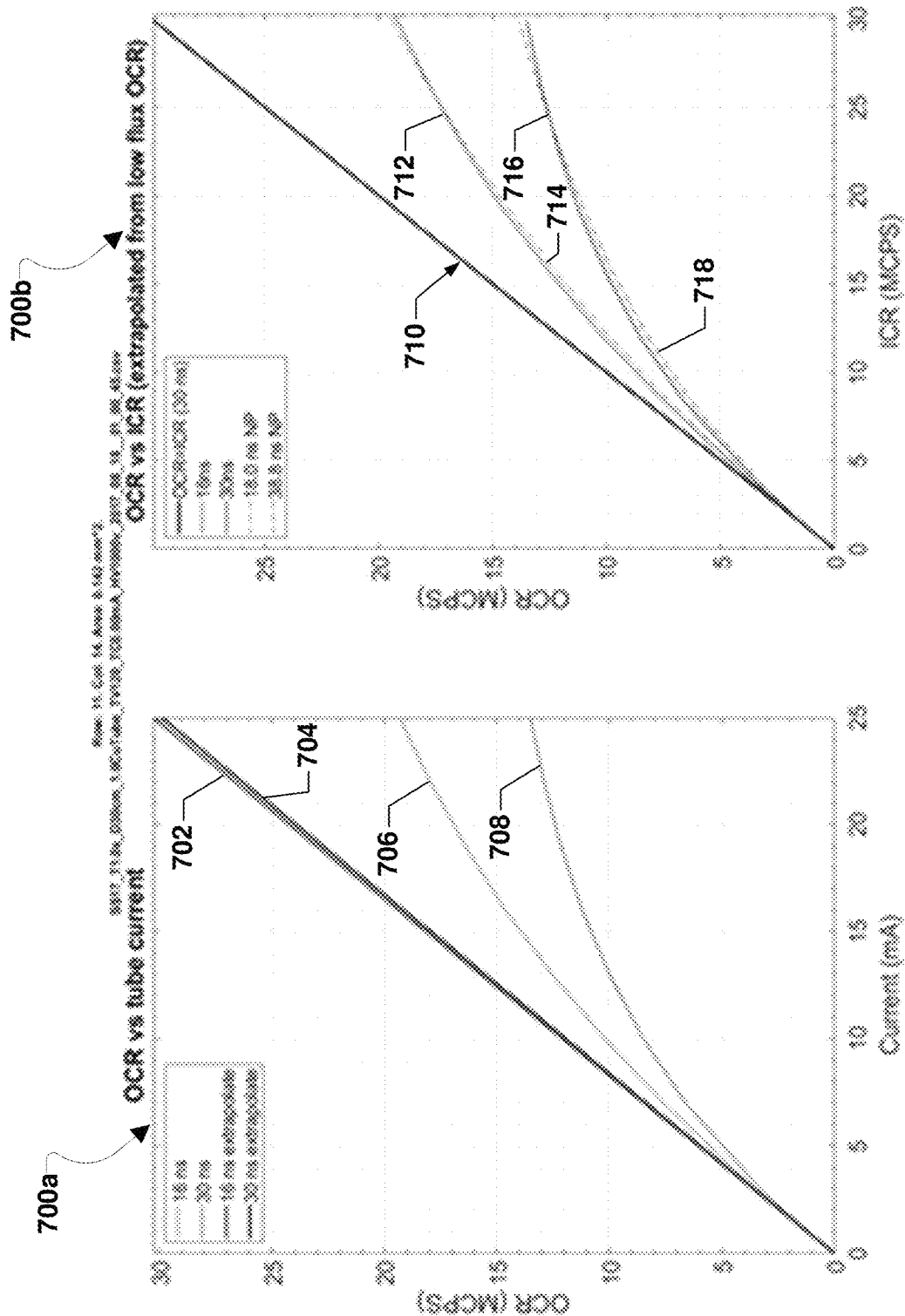
FIGS. 7A and 7B are graphs showing effects of pileup effects in paralyzable and non-paralyzable detectors as a function of the true count rate.

Applying the two-step calibration techniques of the various embodiments to the measured output count rate vs tube current was recoded as shown in FIG. 7A and FIG. 7B. The input Count Rate was extrapolated from low flux output count rate region where the pileup is negligible. The measurements were performed with two different values of the deadtime: 16 ns and 30 ns. The output count rate-input count rate data was then fit into a non-paralyzable model. FIG. 7A shows that the result fits well in both cases (less than 1% deviation). The calibration results are presented in the table shown in FIG. 9 for the case of a 16 ns deadtime. The results for the case of a 30 ns deadtime were very similar. The two-step-based pileup correction factor was applied to the measured data with the results listed in column 4 in the table shown in FIG. 9. Although the calibrated uniformity gets worse with increasing X-ray tube current, the effect is smaller and at an X-ray tube current of 25 mA, a 30% relative improvement from unacceptable 4.9% uniformity metric following the flat field correction step (i.e., down to acceptable 3.3% value) is obtained. Relative improvements in the uniformity metric can be expected to increase at 100 mA (not tested) and extrapolation of the expected results indicates that a uniformity metric of better than 4% can be achieved over the entire range of X-ray tube currents. With better pileup modeling and deadtime extraction the proposed two-step calibration will improve beyond the results summarized in the table shown in FIG. 9. As illustrated in FIGS. 7A and 7B, measured counts of the tested detector matches well to the non-paralyzable model with good agreement for deadtimes of 16 ns and 30 ns, demonstrating that the embodiment methods apply across a wide range of deadtime values.

Figure 10:
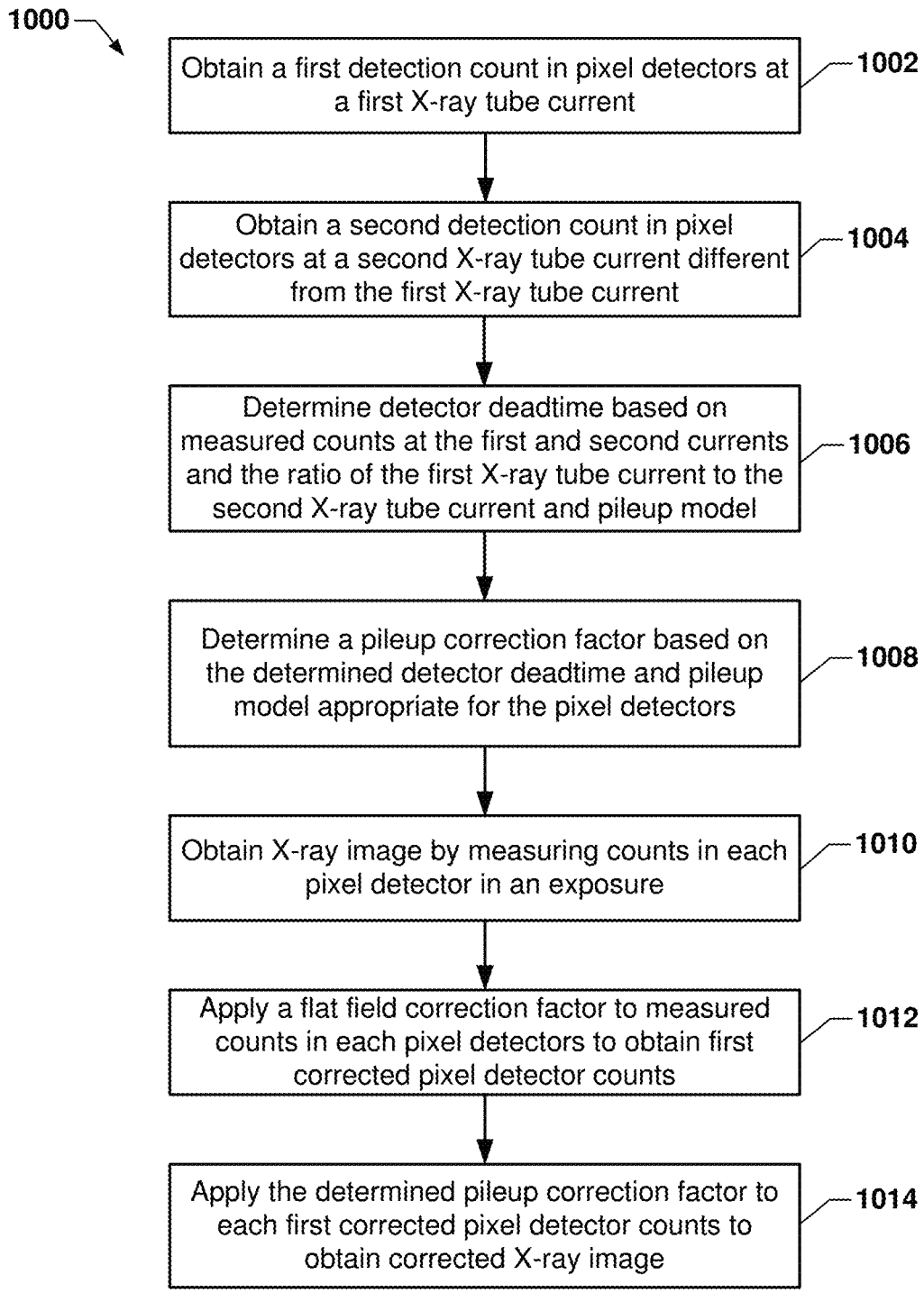
FIG. 10 is a process flow diagram of a method for performing a two-step calibration on a pixelated radiation detector to account for pileup effects according to various embodiments.

FIG. 10 illustrates an embodiment method 1000 for obtaining temporal-spectral information with a pixelated X-ray radiation detector comprising a plurality of detector pixel detectors. The method 1000 may be implemented within a processor of an imaging X-ray detector (e.g., processor 107) or of an X-ray imaging system (e.g., 100) including a radiation detector (e.g., 120, 200) comprised of an array of pixel detectors (e.g., 128, 202). The method 1000 may be performed as part of factory acceptance testing and/or as part of periodic or run-time calibration operations.

In operations of block 1002, the X-ray imaging system may be operated to obtain a first set of detection counts from pixel detectors of the radiation detector while the X-ray tube is operated at a first X-ray tube current for a particular exposure (i.e., period of collecting counts). For example, the X-ray tube current may be operated at 1 mA during these exposures. In some embodiments, count measurements may be obtained from most or all pixel detectors during each exposure. In some embodiments multiple exposures may be obtained and the count measurements may be averaged over multiple exposures to obtain an average of photon detection counts at the first X-ray tube current for a particular exposure. In some embodiments, count measurements may be obtained by a subset of pixel detectors. In some embodiments, count measurements of all pixel detectors may be combined or averaged into a single count measurement of the entire detector.

In operations of block 1004, the X-ray imaging system may be operated to obtain a second set of detection counts from the pixel detectors of the radiation detector while the X-ray tube is operated at a second X-ray tube current for the same exposure time (i.e., same period of collecting counts), in which the second X-ray tube current is different from that of the first X-ray tube current. For example, the X-ray tube current may be operated at 10 mA during these exposures. In some embodiments, count measurements may be obtained from most or all pixel detectors during each exposure. In some embodiments multiple exposures may be obtained and the count measurements may be averaged over multiple exposures to obtain an average of photon detection counts at the first X-ray tube current for a particular exposure. In some embodiments, count measurements may be obtained by a subset of pixel detectors. In some embodiments, count measurements of all pixel detectors may be combined or averaged into a single count measurement of the entire detector.

In operations of block 1006, a processor of the X-ray imaging system (or another processor) may determine the detector system's deadtime based on the measured counts at the first and second X-ray tube currents determined in blocks 1002 and 1004, and the ratio of the first X-ray tube current to the second X-ray tube current using an appropriate pileup model. For example, the processor may use the two measured counts and the ratio of the X-ray tube currents to determine that the deadtime $\tau$, such as using an equation similar to $\tau=(M2-M2/R)^{-1}-(M1*R-M1)^{-1}$.

In operations in block 1008, the processor may use the determined deadtime $\tau$ to determine a pileup correction factor using the appropriate pileup model, such as $(1-M\times\tau)$ as would be appropriate for a detector that exhibits non-paralyzable behavior. The actual correction factor may depend upon the specific behavior exhibited by the detector in response to pileup effects, and may be based on a combination of the paralyzable model and non-paralyzable model described herein.

In operations in block 1010, the X-ray imaging system may obtain an X-ray image by measuring counts in each pixel detector in exposure. For example, an object to be examined may be placed within the X-ray beam between the X-ray tube and the detector module and the X-ray tube operated for an exposure time consistent with conventional imaging methods.

In operations in block 1012, a processor of the X-ray imaging system may apply a flat field correction factor to the measured counts of each of the pixel detectors obtained in block 1010 to obtain first corrected pixel detector counts. Results of this operation is an X-ray image that accounts for static pixel to pixel variability as described herein.

In operations in block 1014, the processor may apply the pileup correction factor determined in block 1008 two each first corrected pixel detector counts to obtain a corrected X-ray image. As described herein this operation corrects for differences in measured versus true counts in each pixel detector due to pileup effects.

Figure 11:
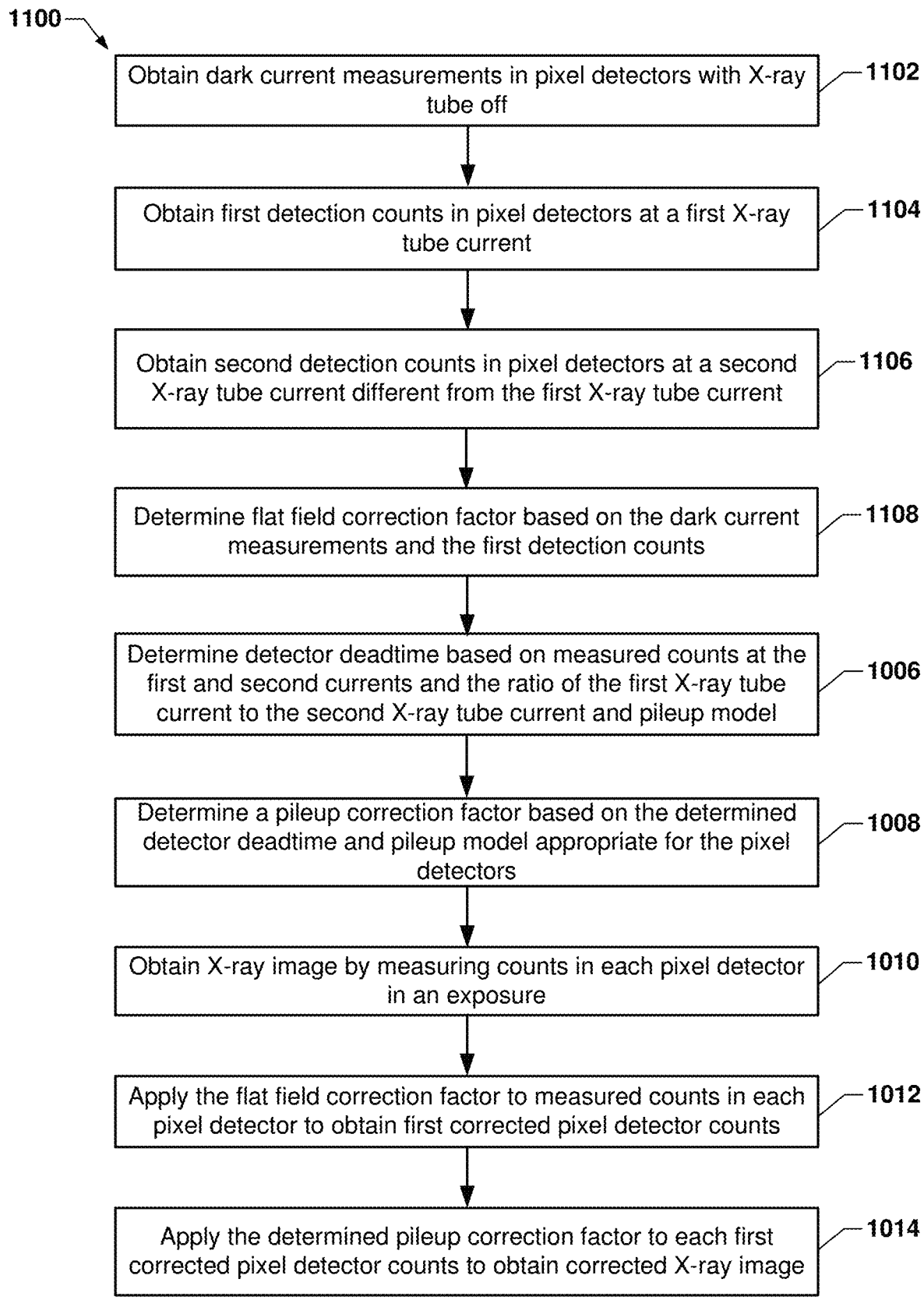
FIG. 11 is a process flow diagram of a method for performing a calibration on a pixelated radiation detector to account for both systemic variability and pileup effects in pixel detector measurements according to various embodiments.

In some embodiments, measurements required to determine the flat field correction may be obtained as part of the same procedure as determining the pileup correction factor. For example, the dark-field measurements (i.e., count measurements taken when the X-ray tube is off) may be obtained prior to (or after) obtaining the count measurements required for determining the deadtime $\tau$ and one of the count measurements may be used in conjunction with the dark-field measurements to determine the flat field calibration. An example of this embodiment is the method 1100 illustrated in FIG. 11. Similar to the method 1000, the method 1100 may be implemented within a processor of an imaging X-ray detector (e.g., processor 107) or of an X-ray imaging system (e.g., 100) including a radiation detector (e.g., 120, 200) comprised of an array of pixel detectors (e.g., 128, 202). The method 1100 may be performed as part of factory acceptance testing and/or as part of periodic or run-time calibration operations.

In the operations of block 1102, the X-ray imaging system may be operated to obtain dark current measurements in pixel detectors with the X-ray tube off. Described above, this measurement obtains dark current noise data from each of the pixel detectors as there are no X-rays passing through the detector materials.

In operations in block 1104, the X-ray imaging system may be operated to obtain a first set of detection counts from pixel detectors of the radiation detector while the X-ray tube is operated at a first X-ray tube current for a particular exposure (i.e., period of collecting counts). In these exposures, the X-ray tube current may be operated at a low level so that the X-ray flux impinging on pixel detectors is low enough to result in minimal pileup events. For example, the X-ray tube current may be operated at 1 mA during these exposures. In some embodiments, count measurements may be obtained from most or all pixel detectors during each exposure. In some embodiments multiple exposures may be obtained and the count measurements may be averaged over multiple exposures to obtain an average of photon detection counts at the first X-ray tube current for a particular exposure. In some embodiments, count measurements may be obtained by a subset of pixel detectors. In some embodiments, count measurements of all pixel detectors may be combined or averaged into a single count measurement of the entire detector.

In operations of block 1106, the X-ray imaging system may be operated to obtain a second set of detection counts from the pixel detectors of the radiation detector while the X-ray tube is operated at a second X-ray tube current for the same exposure time (i.e., same period of collecting counts), in which the second X-ray tube current is different from that of the first X-ray tube current. For example, the X-ray tube current may be operated at 10 mA during these exposures. In some embodiments, count measurements may be obtained from most or all pixel detectors during each exposure. In some embodiments multiple exposures may be obtained and the count measurements may be averaged over multiple exposures to obtain an average of photon detection counts at the first X-ray tube current for a particular exposure. In some embodiments, count measurements may be obtained by a subset of pixel detectors. In some embodiments, count measurements of all pixel detectors may be combined or averaged into a single count measurement of the entire detector.

In operations in block 1108, a processor of the X-ray imaging system (or another processor) may determine a flat field correction factor based on the dark current measurement and the first detection counts. As described above, since the incidence of pileup events is expected below when the X-ray flux is low, determining correction factors that subtract out the dark current and zero out variability in counts from pixel to pixel.

In operations of block 1006, a processor of the X-ray imaging system (or another processor) may determine a detector deadtime based on the measured counts at the first and second X-ray tube currents determined in blocks 1002 and 1004, and the ratio of the first X-ray tube current to the second X-ray tube current using an appropriate pileup model as described for the like numbered block of the method 1000.

In operations in block 1008, the processor may use the determined deadtime τ to determine a pileup correction factor using the appropriate pileup model as described for the like numbered block of the method 1000.

In operations in block 1010, the X-ray imaging system may obtain an X-ray image by measuring counts in each pixel detector in exposure as described for the like numbered block of the method 1000.

In operations in block 1012, a processor of the X-ray imaging system may apply the flat field correction factor (determined in block 1108) to the measured counts of each of the pixel detectors obtained in block 1010 to obtain first corrected pixel detector counts as described for the like numbered block of the method 1000.

In operations in block 1014, the processor may apply the pileup correction factor determined in block 1008 two each first corrected pixel detector counts to obtain a corrected X-ray image as described for the like numbered block of the method 1000.

While various embodiments are described with reference to X-ray imaging detector systems, similar methods of determining correction factors for pileup effects may be implemented for gamma-ray imaging systems. In gamma-ray imaging systems, instead of obtaining count measurements (M1 and M2) at two different X-ray tube currents, count measurements could be obtained using two different gamma flux rates that have a known or calculatable difference ratio. For example, a single gamma-ray source may be used with an attenuation filter between source and detector in one of the measurements, in which the attenuation filter will reduce the gamma-ray flux impinging on the detector array by a known or calculatable amount.

Figure 12:
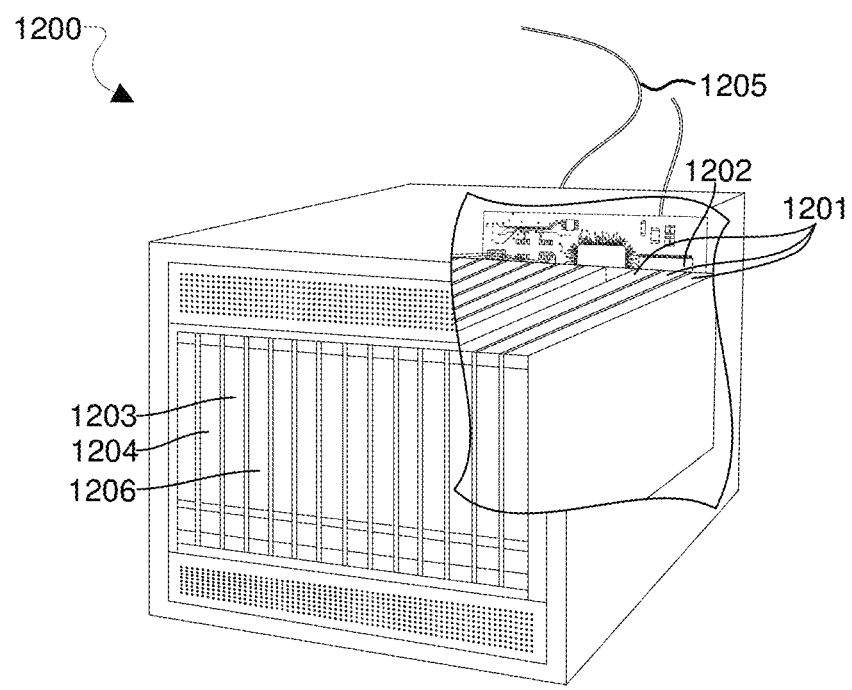
FIG. 12 is a component block diagram illustrating an example server suitable for use with the various embodiments.

The various embodiments (including, but not limited to, the embodiment method described above with reference to FIG. 10) may be implemented in computing systems, such as any of a variety of commercially available computers 1200 as illustrated in FIG. 12. Such a computer 1200 typically includes one or more processors 1201 coupled to volatile memory 1202 and a large capacity nonvolatile memory, such as a disk drive 1204. As illustrated in FIG. 12, one or more processors 1201 may be added to the computer 1200 by inserting them into the racks of the assembly. The computer 1200 may also include a floppy disc drive, compact disc (CD) or digital versatile disc (DVD) disc drive 1206 coupled to the one or more processors 1201. The computer 1200 may also include network access ports 1203 coupled to the one or more processors 1201 for establishing network interface connections with a network 1205, such as a local area network coupled to other computers and servers, or the Internet.

The present embodiments may be implemented in systems used for medical imaging, such as CT imaging, as well as for non-medical imaging applications, such as industrial inspection applications.

Computer program code or executable instructions for execution on a programmable processor for carrying out operations of the various embodiments may be written in a high level programming language such as C, C++, C#, Smalltalk, Java, JavaScript, Visual Basic, a Structured Query Language (e.g., Transact-SQL), Perl, or in various other programming languages. Embodiments may be implemented as program code or processor-executable instructions stored on a non-transitory processor-readable storage medium that are configured to cause a processor coupled to a pixelated radiation detector, such as a processor or analysis unit of an X-ray imaging system, to perform operations of any of the various embodiments. Program code or processor-executable instructions stored on a non-transitory processor readable storage medium as used in this application may refer to machine language code (such as object code) whose format is understandable by a processor. Non-transitory processor-readable storage medium include any form of media used for storing program code or processor-executable instructions including, for example, RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a processor or computer.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:
1. A method of correcting the output from pixel detectors within a pixelated detector of an imaging X-ray system, comprising:
   determining a pileup correction factor based on count measurements obtained at two different X-ray tube current levels; and applying the pileup correction factor to pixel detector count measurements obtained while imaging an object to obtain pixel detector counts corrected for pileup effects;

wherein the determining the pileup correction factor based on count measurements obtained at two different X-ray tube current levels comprises:

obtaining first count measurements in the pixel detectors while operating the imaging X-ray system at a first X-ray tube current level;

obtaining second count measurements in the pixel detectors while operating the imaging X-ray system at a second X-ray tube current level, wherein the second X-ray tube current level is different from the first X-ray tube current level;

using the first and second count measurements and a ratio of the first X-ray tube current level to the second X-ray tube current level to determine a deadtime of the pixelated detector; and determining the pileup correction factor based upon the determine deadtime of the pixelated detector and a pileup model appropriate to a response of the pixelated detector to pileup events.

2. The method of claim 1, wherein the pileup correction factor is equal to $(1-M\times\tau)$, in which M is the measured counts to be corrected and $\tau$ is the determined deadtime of the pixelated detector.

3. The method of claim 1, wherein applying the pileup correction factor to pixel detector count measurements obtained while imaging an object to obtain pixel detector counts corrected for pileup effects comprises:

applying a flat field correction to the pixel detector count measurements obtained while imaging the object to obtain pixel detector counts corrected for pixel-to-pixel variability; and applying the pileup correction factor to the pixel detector counts corrected for pixel-to-pixel variability to obtain pixel detector counts corrected for pileup effects.

4. The method of claim 3, further comprising determining the flat field correction by:

obtaining dark-field noise measurements of the pixel detectors with the X-ray tube off; and determining the flat field correction based on the dark-field noise measurements and the first count measurements.

5. An imaging X-ray detector comprising a plurality of pixel detectors and means for performing functions of the method of claim 1.

6. Circuitry for use with an X-ray detector comprising a plurality of pixel detectors and means for performing functions of the method of claim 1.

7. An imaging X-ray detector, comprising:

a pixelated X-ray detector comprising a plurality of pixel detectors; and a processor configured with processor-executable instructions to perform operations of the method of claim 1.

* * * * *